US012629535B2

(12) United States Patent
Hof et al.

(10) Patent No.: US 12,629,535 B2
(45) Date of Patent: May 19, 2026

(54) PHASE-CHANGE NANOPARTICLE

(71) Applicant: NEW PHASE LTD., Petach Tikva (IL)

(72) Inventors: Raphael Hof, Kfar Yona (IL); Raz Khandadash, Bat Yam (IL); Sarah Kraus, Rishon Le'zion (IL); Pazit Rukenstein, Rishon Le'zion (IL)

(73) Assignee: NEW PHASE LTD., Petach Tikva (IL)

( * ) Notice: Subject to any disclaimer, the term of this patent is extended or adjusted under 35 U.S.C. 154(b) by 1184 days.

(21) Appl. No.: 16/487,299

(22) PCT Filed: Feb. 20, 2018

(86) PCT No.: PCT/IL2018/050190
§ 371 (c)(1),
(2) Date: Aug. 20, 2019

(87) PCT Pub. No.: WO2018/154566
PCT Pub. Date: Aug. 30, 2018

(65) Prior Publication Data
US 2020/0054886 A1 Feb. 20, 2020

Related U.S. Application Data

(60) Provisional application No. 62/461,902, filed on Feb. 22, 2017.

(51) Int. Cl.
*A61N 1/40* (2006.01)
*A61K 9/51* (2006.01)
*A61K 47/02* (2006.01)
*A61P 35/00* (2006.01)

(52) U.S. Cl.
CPC ............ *A61N 1/406* (2013.01); *A61K 9/5115* (2013.01); *A61K 9/5192* (2013.01); *A61K 47/02* (2013.01); *A61P 35/00* (2018.01)

(58) Field of Classification Search
CPC .... A61N 1/406; A61K 9/5115; A61K 9/5192; A61K 47/02; A61K 47/6923; A61K 41/0052; A61P 35/00
See application file for complete search history.

(56) References Cited

U.S. PATENT DOCUMENTS

| | | | |
|---|---|---|---|
| 4,096,616 | A | 6/1978 | Coffinberry |
| 4,106,488 | A | 8/1978 | Gordon |
| 4,204,573 | A | 5/1980 | Clark |
| 4,392,040 | A | 7/1983 | Rand et al. |
| 4,440,217 | A | 4/1984 | Stieler |
| 4,569,836 | A | 2/1986 | Gordon |
| 4,678,460 | A | 7/1987 | Rosner |
| 4,747,826 | A | 5/1988 | Sassano |
| 4,983,159 | A | 1/1991 | Rand |
| 5,003,991 | A | 4/1991 | Takayama |
| 5,217,363 | A | 6/1993 | Brais |
| 5,317,506 | A | 5/1994 | Coutre |
| 5,385,540 | A | 1/1995 | Abbott |
| 5,545,210 | A | 8/1996 | Hess |
| 5,658,234 | A | 8/1997 | Dunlavy |
| 5,667,522 | A | 9/1997 | Flomenblit |
| 5,716,410 | A | 2/1998 | Wang |
| 5,830,179 | A | 11/1998 | Mikus |
| 5,964,744 | A | 10/1999 | Balbierz |
| 5,984,893 | A | 11/1999 | Ward |
| 6,059,810 | A | 5/2000 | Brown |
| 6,120,534 | A | 9/2000 | Ruiz |
| 6,323,459 | B1 | 11/2001 | Maynard |
| 6,390,185 | B1 | 5/2002 | Proeschel |
| 6,451,044 | B1 | 9/2002 | Naghavi et al. |
| 6,576,001 | B2 | 6/2003 | Werneth |
| 6,746,439 | B2 | 6/2004 | Lenker |
| 6,768,921 | B2 | 7/2004 | Organ |
| 6,805,711 | B2 | 10/2004 | Quijano |

(Continued)

FOREIGN PATENT DOCUMENTS

| | | |
|---|---|---|
| CN | 1724135 | 1/2006 |
| CN | 101343529 | 1/2009 |

(Continued)

OTHER PUBLICATIONS

An Office Action together with the English Machine translation dated Aug. 3, 2022, which issued during the prosecution of Chinese Patent Application No. 201880025727.1.
Fan, Xiaoqiao, et al. "Novel Magnetic-to-Thermal Conversion and Thermal Energy Management Composite Phase Change Material." Polymers 10.6 (2018): 585.
An English Translation of an Office Action issued Jan. 20, 2023 in Chinese Application No. 202111575622.3.
An Office Action dated Apr. 20, 2023, which issued during the prosecution of Israel Patent Application. No. IL 268707.
Adolphi NL, Huber DL, Jaetao JE, Bryant HC, Lovato DM, Fegan DL, Venturini EL, Monson TC, Tessier TE, Hathaway HJ, Bergemann C, Larson RS, Flynna ER. Characterization of magnetite nanoparticles for SQUID-relaxometry and magnetic needle biopsy. J Magn Magn Mater (2009) 321:1459-64. doi: 10.1016/j.jmmm.2009.02.067.

(Continued)

*Primary Examiner* — Robert S Cabral
(74) *Attorney, Agent, or Firm* — Sughrue Mion, PLLC

(57) ABSTRACT

Apparatus and methods are described for use with a heating device (26) configured to heat at least a portion of a subject's body. A nanoparticle (22) is configured to be administered to the subject, the nanoparticle including at least one inner core (30) that includes a magnetic material having a Curie temperature; a phase-change-material layer (31) that surrounds the inner core and that comprises a phase-change material that is configured to absorb latent heat of fusion by undergoing a phase change selected from the group consisting of: solid to liquid, and gel to liquid, the phase-change occurring at a phase-change temperature that is lower than the Curie temperature; and an outer layer (32) disposed around the phase-change-material layer, the outer layer comprising a plurality of nano-subparticles (34) that are separated from one another, such as to form a segmented layer. Other applications are also described.

34 Claims, 5 Drawing Sheets

(56) References Cited

U.S. PATENT DOCUMENTS

| | | | |
|---|---|---|---|
| 6,835,858 | B1 | 12/2004 | De Jonge |
| 6,942,637 | B2 | 9/2005 | Cartledge |
| 6,942,644 | B2 | 9/2005 | Worthen |
| 7,041,941 | B2 | 5/2006 | Faries, Jr. |
| 7,074,175 | B2 | 7/2006 | Handy |
| 7,112,273 | B2 | 9/2006 | Weigel |
| 7,117,033 | B2 | 10/2006 | Shalev |
| 7,120,489 | B2 | 10/2006 | Shalev |
| 7,146,209 | B2 | 12/2006 | Gross |
| 7,510,555 | B2 | 3/2009 | Kanzius |
| 7,560,160 | B2 | 7/2009 | Sudarshan |
| 7,627,381 | B2 | 12/2009 | Kanzius |
| 7,731,648 | B2 | 6/2010 | Ivkov |
| 7,919,184 | B2 | 4/2011 | Mohapatra |
| 8,197,471 | B1 | 6/2012 | Tersigni |
| 8,463,397 | B2 | 6/2013 | Munoz Marquez |
| 8,518,870 | B2 | 8/2013 | Harrison, Jr. |
| 8,709,488 | B2 | 4/2014 | Peyman |
| 9,572,695 | B2 | 2/2017 | Hof et al. |
| 9,872,902 | B2 | 1/2018 | Hof et al. |
| 10,172,939 | B2 | 1/2019 | Hof et al. |
| 2002/0183829 | A1 | 12/2002 | Doscher |
| 2004/0059385 | A1 | 3/2004 | Yu |
| 2004/0122494 | A1 | 6/2004 | Eggers |
| 2004/0180086 | A1 | 9/2004 | Ramtoola |
| 2004/0210269 | A1 | 10/2004 | Shalev |
| 2004/0253304 | A1 | 12/2004 | Gross |
| 2005/0033382 | A1 | 2/2005 | Single |
| 2005/0055082 | A1 | 3/2005 | Ben Muvhar |
| 2005/0059928 | A1 | 3/2005 | Larsson |
| 2005/0074506 | A1 | 4/2005 | Natan |
| 2005/0080351 | A1 | 4/2005 | Larsson |
| 2005/0090732 | A1 | 4/2005 | Ivkov et al. |
| 2005/0149170 | A1 | 7/2005 | Tassel et al. |
| 2005/0159790 | A1 | 7/2005 | Shalev |
| 2005/0202310 | A1 | 9/2005 | Yahnker et al. |
| 2005/0283327 | A1 | 12/2005 | Bowman |
| 2005/0288777 | A1 | 12/2005 | Rhee |
| 2006/0020299 | A1 | 1/2006 | Shalev |
| 2006/0074479 | A1 | 4/2006 | Bailey |
| 2006/0083694 | A1 | 4/2006 | Kodas |
| 2006/0194164 | A1 | 8/2006 | Altshuler et al. |
| 2006/0241747 | A1 | 10/2006 | Shaoulian |
| 2006/0276882 | A1 | 12/2006 | Case |
| 2007/0083245 | A1 | 4/2007 | Lamensdorf |
| 2007/0154397 | A1 | 7/2007 | Chang et al. |
| 2007/0264481 | A1 | 11/2007 | DeSimone et al. |
| 2008/0021537 | A1 | 1/2008 | Ben Muvhar |
| 2008/0033509 | A1 | 2/2008 | Shalev |
| 2008/0167700 | A1 | 7/2008 | Shalev |
| 2008/0172102 | A1 | 7/2008 | Shalev |
| 2008/0272331 | A1 | 11/2008 | Mohaparta et al. |
| 2009/0054596 | A1 | 2/2009 | Aoyagi |
| 2009/0082832 | A1 | 3/2009 | Carbunaru et al. |
| 2010/0256708 | A1 | 10/2010 | Thornton et al. |
| 2011/0195526 | A1 | 8/2011 | Su |
| 2012/0221081 | A1 | 8/2012 | Hof et al. |
| 2013/0078288 | A1 | 3/2013 | Yu |
| 2014/0248339 | A1 | 9/2014 | Karathanasis et al. |
| 2015/0112423 | A1 | 4/2015 | Hof et al. |
| 2015/0231282 | A1 | 8/2015 | Pozzo et al. |
| 2016/0281082 | A1* | 9/2016 | Lellouche ............... A61K 47/52 |
| 2016/0361417 | A1* | 12/2016 | Sutermeister ...... A61K 41/0052 |
| 2017/0209580 | A1 | 7/2017 | Hof et al. |
| 2018/0117154 | A1 | 5/2018 | Hof et al. |

FOREIGN PATENT DOCUMENTS

| | | |
|---|---|---|
| CN | 101836915 | 9/2010 |
| CN | 101836915 A | 9/2010 |
| CN | 102172411 | 9/2011 |
| CN | 102198086 | 9/2011 |
| CN | 104127872 A | 11/2014 |
| DE | 19745890 | 3/1999 |
| EP | 0543498 | 5/1993 |
| EP | 0543498 A1 | 5/1993 |
| EP | 2649623 A1 * | 10/2013 ............. A61K 31/12 |
| EP | 2470131 | 11/2014 |
| EP | 3226819 | 10/2018 |
| JP | H03178668 | 8/1991 |
| JP | 2003-509098 | 3/2003 |
| JP | 2003-527924 | 9/2003 |
| JP | 2008-515468 | 5/2008 |
| KR | 10-2018-0002233 A | 1/2018 |
| WO | 94/001165 | 1/1994 |
| WO | 97/26032 | 7/1997 |
| WO | 2000/066192 | 11/2000 |
| WO | 01/019239 | 3/2001 |
| WO | 01/072239 | 10/2001 |
| WO | 02/000145 | 1/2002 |
| WO | 03/028522 | 4/2003 |
| WO | 03/105658 | 12/2003 |
| WO | 2006/022340 A1 | 3/2006 |
| WO | 06/052322 | 5/2006 |
| WO | 2007/107762 | 9/2007 |
| WO | 2008/148014 | 12/2008 |
| WO | 2009/012473 | 1/2009 |
| WO | 2011/024159 | 3/2011 |
| WO | 2015/161211 A1 | 10/2015 |
| WO | 2016/084082 | 6/2016 |
| WO | 2018/154566 | 8/2018 |

OTHER PUBLICATIONS

Albarqi, H. A.; Wong, L. H.; Schumann, C.; Sabei, F. Y.; Korzun, T.; Li, X.; Hansen M. N.; Dhagat, P.; Moses, A. S.; Taratula, O.; and Taratula, O. Biocompatible Nanoclusters with High Heating Efficiency for Systemically Delivered Magnetic Hyperthermia. ACS Nano 2019, 13, 6383-95.

Amoozgar, Z.; Yeo, Y. Recent advances in stealth coating of nanoparticle drug delivery systems. Wiley Interdiscip Rev Nanomed Nanobiotechnol. Mar. 2012 ; 4(2): 219-233.

Anselmo, A. C.; Zhang, M.; Kumar, S.; Vogus, D. R.; Menegatti, S.; Helgeson, M. E.; Mitragotri, S. Elasticity of Nanoparticles Influences Their Blood Circulation, Phagocytosis, Endocytosis, and Targeting. ACS Nano Sep. 3, 2015, 3169-3177.

Arami H, Khandhar A, Liggitt D, Krishnan KM (2015) In vivo delivery, pharmacokinetics, biodistribution and toxicity of iron oxide nanoparticles. Chem Soc Rev 44(23): 8576-8607. https://doi.org/10.1039/c5cs00541h.

Azarmi S, Roa WH, Lobenberg R. Targeted delivery of nanoparticles for the treatment of lung diseases. Adv Drug Deliv Rev (2008) 60:863-75. doi: 10.1016/j.addr.2007.11.006.

Baetke SC, Lammers T, Kiessling F (2015) Applications of nanoparticles for diagnosis and therapy of cancer. Br J Radiol 88(1054):20150207. https://doi.org/10.1259/bjr.20150207.

Bae, K. H.; Ha, Y. J.; Kim, C.; Lee, K-R.; Park, T. G. Pluronic/chitosan shell cross-linked nanocapsules encapsulating magnetic nanoparticles. J. Biomater. Sci. Polymer Edn, vol. 19, No. 12, pp. 1571-1583 (2008).

Breitenkamp, K.; Emrick, T. Novel Polymer Capsules from Amphiphilic Graft Copolymers and Cross-Metathesis. J. Am. Chem. Soc. 2003, 125, 12070-12071.

Bohorquez, M.; Koch, C.; Trygstad, T.; Pandit, N. A Study of the Temperature-Dependent Micellization of Pluronic F127. J. Colloid Interface Sci. 1999, 216, 34-40.

Cervadoro, A.; Cho, M.; Key, J.; Cooper, C.; Stigliano, C.; Aryal, S.; Brazdeikis, A.; Leary J. F.; Decuzzi, P. Synthesis of Multifunctional Magnetic Nanoflakes for Magnetic Resonance Imaging, Hyperthermia, and Targeting. ACS Appl. Mater. Interfaces Jun. 2014, 12939-46.

Chen F, Ehlerding EB, Cai W. Theranostic nanoparticles. J Nucl Med. Dec. 2014;55(12):1919-22. Epub Nov. 20, 2014. PMID: 25413134; PMCID: PMC4255955.

Creixell, M.; Bohorquez, A. C.; Torres-Lugo, M.; Rinaldi, C. EGFR-Targeted Magnetic Nanoparticle Heaters Kill Cancer Cells without a Perceptible Temperature Rise. ACS Nano May 2011, 7124-7129.

(56) References Cited

OTHER PUBLICATIONS

Dai, Q.; Wilhelm, S.; Ding, D.; Syed, A. M.; Sindhwani, S.; Zhang, Y.; Chen, Y. Y.; MacMillan, P.; Chan, W. C. W. Quantifying the Ligand-Coated Nanoparticle Delivery to Cancer Cells in Solid Tumors. ACS Nano Dec. 2018, 8423-8435.

Das, R.; Alonso, J.; Nemati Porshokouh, Z.; Kalappattil, V.; Torres, D.; Phan, M. H.; Garaio, E.; Garcia, J. A.; Sanchez Llamazares, J. L.; Srikanth, H. Tunable High Aspect Ratio Iron Oxide Nanorods for Enhanced Hyperthermia. J. Phys. Chem. C 2016, 120, 10086-93.

De la Presa, P.; Luengo, Y.; Multigner, M.; Costo, R.; Morales, M. P.; Rivero, G.; Hernando, A. Study of Heating Efficiency as a Function of Concentration, Size, and Applied Field in γ Fe2O3 Nanoparticles. J. Phys. Chem. C 2012, 116, 25602-10.

Denardo SJ, Denardo GL, Miers LA, Natarajan A, Foreman AR, Gruettner C, Adamson GN, Ivkov R. Development of tumor targeting bioprobes ((111) in-chimeric L6 monoclonal antibody nanoparticles for alternating magnetic field cancer therapy. Clin. Cancer Res (2005) 11(19 Pt 2):7087s-7092s. doi: 10.1158/1078-0432.CCR-1004-0022.

Derfus, A. M.; von Maltzahn, G.; Harris, T. J.; Duza, T.; Vecchio, K. S.; Ruoslahti, E.; Bhatia, S. N. Remotely Triggered Release from Magnetic Nanoparticles. Adv. Mater. 2007, 19, 3932-36.

Dutz, S.; Hergt, R. Magnetic Nanoparticle Heating and Heat Transfer on a Microscale: Basic Principles, Realities and Physical Limitations of Hyperthermia for Tumour Therapy. Int. J. Hyperthermia 2013, 29, 790-800.

Ebrahimi, M. On the Temperature Control in Self-Controlling Hyperthermia Therapy. J. Magn. Magn. Mater. 2016, 416, 134-140.

Edge D, Shortt CM, Gobbo OL, Teughels S , Prina-Mello A, Volkov Y, MacEneaney P, Radomski MW, Markos F (2016) Pharmacokinetics and bio-distribution of novel super paramagnetic iron oxide nanoparticles (SPIONs) in the anaesthetized pig. Clin Exp Pharmacol Physiol 43(3):319-326. https://doi.org/10.1111/1440-1681.12533.

Fam, Y.; Chee, C. F.; Yong, C. Y.; Ho, K. L.; Mariatulqabtiah, A. R. Tan, W. Stealth Coating of Nanoparticles in Drug-Delivery Systems. Nanomaterials Oct. 2020, 787.

Feng Q, Liu Y, Huang J, Chen K, Huang J, Xiao K (2018) Uptake, distribution, clearance, and toxicity of iron oxide nanoparticles with different sizes and coatings. Sci Rep 8(1):2082. https://doi.org/10.1038/s41598-018-19628-z.

Ferrari, R.; Sponchioni, M.; Morbidellia, M.; Moscatelli, D. Polymer nanoparticles for the intravenous delivery of anticancer drugs: the checkpoints on the road from the synthesis to clinical translation. Nanoscale, Oct. 2018, 22701-22719.

Gneveckow U, Jordan A, Scholz R, Brüss V, Waldöfner N, Ricke J, Feussner A, Hildebrandt B, Rau B, Wust P (2004) Description and characterization of the novel hyperthermia- and thermoablation-system MFH® 300F for clinical magnetic fluid hyperthermia. Med Phys 31(6):1444-51. https://doi.org/10.1118/1.1748629.

Gonzales, M.; Krishnan, K. M. Phase transfer of highly monodisperse iron oxide nanocrystals with Pluronic F127 for biomedical applications. J. Magn. Magn. Mater. 311 (2007) 59-62.

Gordon, R. T.; Hines, J. R.; Gordon, D. Intracellular Hyperthermia. A Biophysical Approach to Cancer Treatment via Intracellular Temperature and Biophysical Alterations. Med. Hypotheses May 1979, 5 83-102.

Greish K. Enhanced permeability and retention (EPR) effect for anticancer nanomedicine drug targeting. Methods Mol Biol (2010) 624:25-37. doi: 10.1007/978-1-60761-609-2_3.

Guo, P.; Liu, D.; Subramanyam, K.; Wang, B.; Yang, J.; Huang, J.; Auguste, D. T.; Moses, M. A. Nanoparticle elasticity directs tumor uptake. Nat. Commun (2018) 9:130.

Hergt R, Dutz S (2007) Magnetic particle hyperthermia—Biophysical limitations of a visionary tumor therapy. J Mag Mag Mater 311:187-192.

Hirn S, Semmler-Behnke M, Schleh C, Wenk A, Lipka J, Schäffler M, Takenaka S, Möller W, Schmid G, Simon U, Kreyling WG. Particle size-dependent and surface charge dependent biodistribution of gold nanoparticles after intravenous administration. Eur J Pharm Biopharm (2011) 77: 407-416. doi: 10.1016/j.ejpb.2010.12.029.

Ho JC, Nguyen L, Law JJ, Ware MJ, Keshishian V, Lara NC, Nguyen T, Curley SA, Corr SJ (2017) Non-invasive radiofrequency field treatment to produce hepatic hyperthermia: Efficacy and safety in swine. IEEE J Transl Eng Health Med 5:1500109. https://doi.org/10.1109/JTEHM.2017.2672965.

Huang, H. S.; Hainfeld, J. F. Intravenous Magnetic Nanoparticle Cancer Hyperthermia. Int. J. Nanomed. Aug. 2013, 2521-32.

Ito, A.; Tanaka, K.; Kondo, K.; Shinkai, M.; Honda, H.; Matsumoto, K.; Saida, T.; Kobayashi, T. Tumor Regression by Combined Immunotherapy and Hyperthermia Using Magnetic Nanoparticles in an Experimental Subcutaneous Murine Melanoma. Cancer Sci. 2003, 94, 308-13.

Ivkov R, DeNardo SJ, Daum W, Foreman AR, Goldstein RC, Nemkov VS, DeNardo GL (2005) Application of high amplitude alternating magnetic fields for heat induction of nanoparticles localized in cancer. Clin Cancer Res 11(19 Pt 2):7093s-7103s. https://doi.org/10.1158/1078-0432.CCR-1004-0016.

Jain S, Hirst DG, O'Sullivan JM. Gold nanoparticles as novel agents for cancer therapy. Br J Radiol (2012) 85:101-13. doi: 10.1259/bjr/59448833.

Jain, T. K.; Foy, S. P.; Erokwu, B.; Dimitrijevic, S.; Flask, C. A.; Labhasetwar, V. Magnetic resonance imaging of multifunctional pluronic stabilized iron-oxide nanoparticles in tumor-bearing mice. Biomaterials 30 (2009) 6748-6756.

Jain TK, Reddy MK, Morales MA, Leslie-Pelecky DL, Labhasetwar V (2008) Biodistribution, clearance, and biocompatibility of iron oxide magnetic nanoparticles in rats. Mol Pharm 5(2):316-327. https://doi.org/10.1021/mp7001285.

Jean-Paul, F.; Claire, W.; Jacques, S.; Christine, M.; Jean-Claude, B.; Florence, G. Size-Sorted Anionic Iron Oxide Nanomagnets as Colloidal Mediators for Magnetic Hyperthermia J. Am. Chem. Soc. 2007, 129, 2628-2635.

Johannsen M, Thiesen B, Wust P, Jordan A (2010) Magnetic nanoparticle hyperthermia for prostate cancer. Int J Hyperthermia 26(8):790-795. https://doi.org/10.3109/02656731003745740.

Keblinski, P.; Cahill, D. G.; Bodapati, A.; Sullivan, C. R.; Taton, T. A. Limits of Localized Heating by Electromagnetically Excited Nanoparticles. J. Appl. Phys. 2006, 100, 054305.

Khandadash, R.; Machtey, V.; Shainer, I.; Gottlieb, H. E.; Gothilf, Y.; Ebenstein, Y.; Weiss, A.; Byk, G. Novel Biocompatible Hydrogel Nanoparticles: Generation and Size-Tuning of Nanoparticles by the Formation of Micelle Templates Obtained from Thermo-Responsive Monomers Mixtures. J. Nanopart. Res. 2014, 16, 2796.

Krasia-Christoforou, T.; Socoliuc, V.; Knudsen, K. D.; Tombacz, E.; Turcu, R.; Vekas, L. From Single-Core Nanoparticles in Ferrofluids to Multi-Core Magnetic Nanocomposites: Assembly Strategies, Structure, and Magnetic Behavior. Nanomaterials Oct. 2020, 2178.

Lanier, O. I.; Korotych, O. I.; Monsalve, A. G.; Wable, D.; Savliwala, S.; Grooms, N. W. F.; Nacea, C.; Tuitt, O. R.; Dobson, J. Evaluation of Magnetic Nanoparticles for Magnetic Fluid Hyperthermia. Int. J. Hyperthermia 2019, 36, 686-700.

Lee, J. h.; Jang, J. t.; Choi, J. s.; Moon, S. H.; Noh, S. h.; Kim, J. w.; Kim, J-G.; Kim, I. s.; Park, K. I.; Cheon, J. Exchange-Coupled Magnetic Nanoparticles for Efficient Heat Induction. Nat. Nanotechnol. Jun. 2011, 418-22.

Lee, N.; Yoo, D.; Ling, D.; Cho, M. H.; Hyeon, T.; Cheon, J.; Iron Oxide Based Nanoparticles for Multimodal Imaging and Magnetoresponsive Therapy. Chem. Rev. 2015, 115, 10637-10689.

Letchford, K.; Burt, H. A review of the formation and classification of amphiphilic block copolymer nanoparticulate structures: micelles, nanospheres, nanocapsules and polymersomes. Eur. J. Pharm. Biopharm. 65 (2007) 259-269.

Li, B.; Chu, F.; Lu, Q.; Wang, Y.; Lane, L. A. Alternating Stealth Polymer Coatings Between Administrations Minimizes Toxic and Antibody Immune Responses towards Nanomedicine Treatment Regimens. Acta Biomater. 2021, 121, 527-540.

Li K, Nejadnik H, Daldrup-Link HE. Next-generation superparamagnetic iron oxide nanoparticles for cancer theranostics. Drug Discov Today. Sep. 2017;22(9):1421-1429. Epub Apr. 26, 2017. PMID: 28454771; PMCID: PMC5610947.

(56)             References Cited

OTHER PUBLICATIONS

Liu X, Zhang Y, Wang Y, Zhu W, Li G, Ma X, Zhang Y, Chen S, Tiwari S, Shi K, Zhang S, Fan HM, Zhao YX, Liang XJ. Comprehensive understanding of magnetic hyperthermia for improving antitumor therapeutic efficacy. Theranostics. Feb. 19, 2020;10(8):3793-3815. PMID: 32206123; PMCID: PMC7069093.

Liu, X.; Zheng, J.; Sun, W.; Zhao, X.; Li, Y.; Gong, N.; Wang, Y.; Ma, X.; Zhang, T.; Zho, L. Y.; Hou, Y.; Wu, Z.; Du, Y.; Fan, H.; Tian, J.; Liang, X.-J. Ferrimagnetic Vortex Nanoring-Mediated Mild Magnetic Hyperthermia Imparts Potent Immunological Effect for Treating Cancer Metastasis. ACS Nano 2019, 13, 8811-25.

Maeda H, Bharate GY, Daruwalla J. Polymeric drugs and nanomedicines for efficient tumor targeted drug delivery based on EPR effect. Eur J Pharm Biopharm (2009) 71:409-19. doi: 10.1016/j.ejpb.2008.11.010.

Mahmoudi M, Hosseinkhani H, Hosseinkhani M, Boutry S, Simchi A, Journeay WS, Subramani K, Laurent S. Magnetic resonance imaging tracking of stem cells in vivo using iron oxide nanoparticles as a tool for the advancement of clinical regenerative medicine. Chem Rev (2011) 111:253-80. doi: 10.1021/cr1001832.

Mahmoudi, K.; Bouras, A.; Bozec, D.; Ivkov, R.; Hadjipanayis, C. Magnetic Hyperthermia Therapy for the Treatment of Glioblastoma: A Review of the Therapy's History, Efficacy and Application in Humans. Int. J. Hyperthermia 2018, 34, 1316-1328.

Maier-Hauff K, Rothe R, Scholz R, Gneveckow U, Wust P, Thiesen B, Feussner A, von Deimling A, Waldoefner N, Felix R, Jordan A (2007). Intracranial thermotherapy using magnetic nanoparticles combined with external beam radiotherapy: Results of a feasibility study on patients with glioblastoma multiforme. J Neurooncol 81:53-60.

Maier-Hauff, K.; Ulrich, F.; Nestler, D.; Niehoff, H.; Wust, P.; Thiesen, B.; Orawa, H.; Budach, V.; Jordan, A. Efficacy and Safety of Intratumoral Thermotherapy Using Magnetic Iron-Oxide Nanoparticles Combined with External Beam Radiotherapy on Patients with Recurrent Glioblastoma Multiforme. J. Neuro-Oncol. 2011, 103, 317-324.

Martinez-Boubeta, C.; Simeonidis, K.; Makridis, A.; Angelakeris, M.; Iglesias, O.; Guardia, P.; Cabot, A.; Yedra, L.; Estradé, S.; Peiró, F.; Saghi, Z.; Midgley, P. A.; Conde-Leborán, I.; Serantes, D.; Baldomir, D. Learning from Nature to Improve the Heat Generation of Iron-Oxide Nanoparticles for Magnetic Hyperthermia Applications. Sci. Rep. Mar. 1-8, 2013.

Miao, L.; Liu, F.; Lin, S.; Hu, J.; Liu, G.; Yang, Y.; Tu, Y.; Hou, C.; Li, F.; Hu, M.; Luo, H. Superparamagnetic-Oil-Filled Nanocapsules of a Ternary Graft Copolymer. Langmuir 2014, 30, 3996-4004.

Moghimi SM, Simberg D (2017) Complement activation turnover on surfaces of nanoparticles. Nano Today 15: 8-10. https://doi.org 10.1016/j.nantod.2017.03.001.

Morales, M. A.; Kumar Jain, T.; Labhasetwar, V.; Leslie-Pelecky, D. L. Magnetic studies of iron oxide nanoparticles coated with oleic acid and Pluronic® block copolymer. Journal of Applied Physics 97, 10Q905 (2005).

Nakamura Y, Mochida A, Choyke PL, Kobayashi H. Nanodrug delivery: Is the enhanced permeability and retention effect sufficient for curing cancer? Bioconjug Chem (2016) 27:2225-2238. doi: 10.1021/acs.bioconjchem.6b00437.

Nelson NR, Port JD, Pande MK. Use of Superparamagnetic Iron Oxide Nanoparticles (SPIONs) via Multiple Imaging Modalities and Modifications to Reduce Cytotoxicity: An Educational Review. Journal of Nanotheranostics; Accepted: Dec. 4, 2020; Published: Dec. 9, 2020.

Ortgies, D. H.; Teran, F. J.; Rocha, U.; de la Cueva, L.; Salas, G.; Cabrera, D.; Vanetsev, A. S.; Rähn, M.; Sammelselg, V.; Orlovskii, Y. V.; Jaque, D. Optomagnetic Nanoplatforms for In Situ Controlled Hyperthermia. Adv. Funct. Mater. 2018, 28, 1704434.

Owens DE, Peppas NA. Opsonization, biodistribution, and pharmacokinetics of polymeric nanoparticles. Int J Pharm (2006) 307:93-102. doi: 10.1016/j.ijpharm.2005.10.010.

Pandey, S.; Quetz, A.; Aryal, A.; Dubenko, I.; Mazumdar, D.; Stadler, S.; Ali, N. Thermosensitive Ni-based Magnetic Particles for Self-Controlled Hyperthermia Applications. J. Magn. Magn. Mater. 2017, 427 ,200-205.

Park EJ, Oh SY, Kim Y, Yoon C, Lee BS, Kim SD, Kim JS. Distribution and immunotoxicity by intravenous injection of iron nanoparticles in a murine model. J Appl Toxicol (2016) 36:414-23. doi: 10.1002/jat.3232.

Peer D, Karp JM, Hong S, Farokhzad OC, Margalit R, Langer R. Nanocarriers as an emerging platform for cancer therapy. Nat Nanotechnol. Dec. 2007;2(12):751-60. PMID: 18654426.

Rabanel, J.-M.; Hildgen, P.; Banquy, X. Assessment of PEG on Polymeric Particles Surface, a Key Step in Drug Carrier Translation. J. Controlled Release 2014, 185, 71-87.

Riedinger, A.; Guardia, P.; Curcio, A.; Garcia, M. A.; Cingolani, R.; Manna, L.; Pellegrino, T. Subnanometer Local Temperature Probing and Remotely Controlled Drug Release Based on Azo-Functionalized Iron Oxide Nanoparticles. Nano Lett 2013 13, 2399-406.

Russo, E.; Villa, C. Poloxamer Hydrogels for Biomedical Applications. Pharmaceutics Nov. 2019, 671.

Sar, A.; Alkan, C.; Kahraman, D. K.; Cinar Kızıl. Micro/Nano Encapsulated n-Tetracosane and n-Octadecane Eutectic Mixture with Polystyrene Shell for Low-Temperature Latent Heat Thermal Energy Storage Applications. Sol. Energy 2015, 115-195-203.

Sasikala, A. R. K.; Thomas, R. G.; Unnithan, A. R.; Saravanakumar, B.; Jeong, Y. Y.; Park, C. H.; Kim, C. S. Multifunctional Nanocarpets for Cancer Theranostics: Remotely Controlled Graphene Nanoheaters for Thermo-Chemosensitisation and Magnetic Resonance Imaging. Sci. Rep. Jun. 2016, 20543.

Sharma A, Tyagi VV, Chen CR, Buddhi D (2009) Review on thermal energy storage with phase change materials and applications. Renew Sustain Energ Rev 13: 318-345. https://doi.org/10.1016/j.rser.2007.10.005.

Sharma, S. K.; Shrivastava, N.; Rossi, F.; Tung, L. D.; Thanh, N. T. K. Nanoparticles-Based Magnetic and Photo Induced Hyperthermia for Cancer Treatment. Nano Today 2019, 29, 100795.

Siemann, D. W. The Unique Characteristics of Tumor Vasculature and Preclinical Evidence for its Selective Disruption by Tumor-Vascular Disrupting Agents. Cancer Treat. Rev. 2011, 37, 63-74.

Stigliano, R. V.; Shubitidze, F.; Petryk, J. D.; Shoshiashvili, L.; Petryk, A. A.; Hoopes, P. J. Mitigation of Eddy Current Heating During Magnetic Nanoparticle Hyperthermia Therapy. Int. J. Hyperthermia 2016, 32, 735-748.

Sun, C.; Du, Kim.; Fang, C.; Bhattarai, N.; Veiseh, O.; Kivit, F.; Stephen, Z.; Lee, D.; Ellenbogen, R. G.; Ratner, B.; Zhang, M. PEG-Mediated Synthesis of Highly Dispersive Multifunctional Superparamagnetic Nanoparticles: Their Physicochemical Properties and Function In Vivo. ACS Nano Apr. 2010, 2402-10.

Suriyanto; Ng, E. Y. K.; Kumar, S. D. Physical Mechanism and Modeling of Heat Generation and Transfer in Magnetic Fluid Hyperthermia through Neelian and Brownian Relaxation: a Review. Biomed. Eng. Online. 2017, 16, 36.

Sykes, E. A.; Chen, J.; Zheng, G.; Chan, W. C. Investigating the Impact of Nanoparticle Size on Active and Passive Tumor Targeting Efficiency. ACS Nano Aug. 2014, 5696-5706.

Tansi FL, Maduabuchi WO, Hirsch M, Southern P, Hattersley S, Quaas R, Teichgräber U, Pankhurst QA, Hilger I (2021) Deep-tissue localization of magnetic field hyperthermia using pulse sequencing. Int J Hyperthermia 38(1):743-54.

Tombácz, E.; Turcu, R.; Socoliuc, V.; Vekas, L. Magnetic iron oxide nanoparticles: Recent trends in design and synthesis of magnetoresponsive nanosystems. Biochem. Biophys. Res. Commun. 468 (2015) 442-453.

Tong, S.; Quinto, C. A.; Zhang, L.; Mohindra, P.; Bao, G. The Size-Dependent Heating of Magnetic Iron Oxide Nanoparticles. ACS Nano Nov. 2017, 6808-16.

Tsoi KM, MacParland SA, Ma XZ, Spetzler VN, Echeverri J, Ouyang B, Fadel SM, Sykes EA, Goldaracena N, Kaths JM, Conneely JB, Alman BA, Selzner M, Ostrowski MA, Adeyi OA, Zilman A, McGilvray ID, Chan WC. Mechanism of hard-nanomaterial clearance by the liver. Nat Mater (2016) 15:1212-21. doi: 10.1038/nmat4718.

(56) References Cited

OTHER PUBLICATIONS

Vreeland, E. C.; Watt, J.; Schober, G. B.; Hance, B. G.; Austin, M. J.; Price, A. D.; Fellows, B. D.; Monson, T. C.; Hudak, N. S.; Maldonado-Camargo, L.; Bohorquez, A. C.; Rinaldi, Carlos.; Huber, D. L. Enhanced Nanoparticle Size Control by Extending LaMer's Mechanism. Chem. Mater. 2015, 27, 6059-66.

Wetterskog, E.; Castro, A.; Zeng, L.; Petronis, S.; Heinke, D.; Olsson, E.; Nilsson, L.; Gehrke, N.; Svedlindh, P. Size and Property Bimodality in Magnetic Nanoparticle Dispersions: Single Domain Particles vs. Strongly Coupled Nanoclusters. Nanoscale Sep. 2017, 4227-35.

Wilhelm S, Tavares AJ, Dai Q, Ohta S, Audet J, Dvorak HF, Chan, WC. Analysis of nanoparticle delivery to tumors. Nat Rev Mat (2016) 1: 16014. doi: 10.1038/natrevmats.2016.14.

Wust P, Gneveckow U, Johannsen M, Böhmer D, Henkel T, Kahmann F, Sehouli J, Felix R, Ricke J, Jordan A (2006) Magnetic nanoparticles for interstitial thermotherapy—feasibility, tolerance and achieved temperatures. Int J Hyperthermia 22(8):673-685. https://doi.org/10.1080/02656730601106037.

Wust P, Hildebrandt B, Sreenivasa G, Rau B, Gellermann J, Riess H, Felix R, Schlag PM. Hyperthermia in combined treatment of cancer. Lancet Oncol (2002) 3:487-97. doi: 10.1016/S1470-2045(02)00818-5.

Yang L, Kuang H, Zhang W, Aguilar ZP, Wei H, Xu H. Comparisons of the biodistribution and toxicological examinations after repeated intravenous administration of silver and gold nanoparticles in mice. Sci Rep (2017) 7: 3303. doi: 10.1038/s41598-017-03015-1.

Zhang, W.; Gilstrap, K.; Wu, L.; Bahadur K. C., R.; Moss, M. A.; Wang, Q.; Lu, X.; He, X. Synthesis and Characterization of Thermally Responsive Pluronic F127-Chitosan Nanocapsules for Controlled Release and Intracellular Delivery of Small Molecules. ACS Nano Apr. 2010, 6747-59.

Zhang, W.; Zuo, X.; Niu, Y.; Wu, C.; Wang, S.; Guanb, S.; Silva, S. R. P. Novel Nanoparticles with Cr3+ Substituted Ferrite for Self-Regulating Temperature Hyperthermia. Nanoscale Sep. 2017, 13929-37.

U.S. Appl. No. 61/275,068, filed Aug. 24, 2009.

U.S. Appl. No. 61/275,071, filed Aug. 24, 2009.

U.S. Appl. No. 61/275,089, filed Aug. 24, 2009.

An International Preliminary Report on Patentability dated Feb. 28, 2012, which issued during the prosecution of Applicant's PCT/IL2010/000683.

An International Search Report and a Written Opinion both dated Feb. 18. 2011, which issued during the prosecution of Applicant's PCT/IL2010/000683.

U.S. Appl. No. 62/083,978, filed Nov. 25, 2014.

An Office Action dated April 6. 2018, which issued during the prosecution of U.S. Appl. No. 14/579,340.

Cryotherapy: A Novel Treatment Option for Prostate Cancer Article dated Aug. 12, 2008 from www.galilmedical.com.

Cancer's Molecular Sweet Tooth and the Warburg Effect, by Kim, Cancer Res 2006; 66: (18). Sep. 15, 2006.

An Office Action dated October 5. 2017, which issued during the prosecution of U.S. Appl. No. 14/579,340.

An Office Action dated Feb. 5, 2019, which issued during the prosecution of U.S. Appl. No. 14/579,340.

Golden slingshot, The Economist, Nov. 6, 2008.

"Lipase-catalysed synthesis of glucose fatty acid esters in tert-butanol," by Degn, Biotechnology Letters 21: 275-280, 1999.

An International Preliminary Report on Patentability dated May 30, 2017, which issued during the prosecution of Applicant's PCT/IL2015/051146.

An Office Action dated Mar. 22, 2018, which issued during the prosecution of U.S. Appl. No. 15/852,293.

"Optimization of Carbohydrate Fatty Acid Ester Synthesis in Organic Media by a Lipase from Candida antarctica," by Degn, Biotechnology and Bioengineering, vol. 74, No. 6, Sep. 20, 2001.

Fluorodeoxyglucose, Wikipedia entry dated Jan. 18, 2009.

"Pathologic analysis of photothermal and photomechanical effects of laser-tissue interactions," by Thomsen, Photochem Photobiol. Jun. 1991;53(6):825-35.

Applied Thermal Engineering, Zalba et al., 23(3), Feb. 2003, pp. 251-283.

Notice of Allowance dated Sep. 18, 2017, which issued during the prosecution of U.S. Appl. No. 15/478,849.

Fajardo et al. "Effects of Hyperthermia in a Malignant Tumor", Cancer 45: 613-623 (1980).

Short et al. "Physical Hyperthermia and Cancer Therapy" Proceedings of the IEEE 68: 133-142 (1980) p. 136 col. 2 para 6.

Notice of Allowance dated December 5. 2016, which issued during the prosecution of U.S. Appl. No. 13/392,037.

An Office Action dated Apr. 8, 2015, which issued during the prosecution of U.S. Appl. No. 13/392,037.

An Office Action dated Aug. 19, 2014, which issued during the prosecution of U.S. Appl. No. 13/392,037.

Notice of Allowance dated Aug. 1, 2019, which issued during the prosecution of U.S. Appl. No. 14/579,340.

An Extended European Search Report dated Mar. 20, 2013, which issued during the prosecution of European Patent Application No. 10811360.

Database Impact [Online] the institute of electrical engineers, Stevenage, GB: Jan. 1, 2009, Huang Yong et al., "Preparation and Characterization of magnetic phase-change microcapsules", XP002693430 Database accession No. 11184663 (abstract).

An English translation of an Office Action dated Apr. 8, 2014 which issued during the prosecution of Japanese Patent Application No. 526180/2012.

De Jong et al. "Particle size-dependent organ distribution of gold nanoparticles after intravenous administration" Published: Feb. 2008 Biomaterials 29 (2008) 1912-1919.

"Energy Absorption of Gold Nanoshells in Hyperthermia Therapy" Published: Aug. 2008 NanoBioscience, IEEE Transactions on, Issue Date: Sep. 2008, Written by: Changhong Liu; Mi, C.C.; Li, B.Q.

Shenoi et al. "Nanoparticle Pre-Conditioning for Enhanced Thermal Therapies in Cancer" Published: Apr. 2011 Nanomedicine (Lond). Apr. 2011 ; 6(3): 545-563.

Yonggang Lv, et al. "Theoretical model for thermal protection by microencapsulated phase change micro/nanoparticles during hyperthermia" Published: Sep. 2011 Heat Mass Transfer (2012) 48:573-584.

Int. J. Hyperthermia, Jan. 11, 2005, preview article, by Johannsen et al. "Clinical hyperthermia of prostate cancer using magnetic nanoparticles: Presentation of a new interstitial technique" Published: Nov. 2005.

Robby Petros et al. "Strategies in the design of nanoparticles for therapetuic applications" Published: Jul. 2010 Nature Reviews Drug Discovery 9, 615-627 (Aug. 2010).

European Search Report dated Mar. 13, 2015, which issued during the prosecution of Applicant's European App No. 14192528.9.

European Search Report dated Jul. 9, 2015, which issued during the prosecution of Applicant's European App No. 14192528.9.

An Office Action dated Dec. 11, 2015, which issued during the prosecution of U.S. Appl. No. 13/392,037.

An Office Action dated May 16, 2016, which issued during the prosecution of U.S. Appl. No. 13/392,037.

Minghui Zhang et al: "Encapsulated nano-heat-sinks for thermal management of heterogeneous chemical reactions", Nanoscale, vol. 2, No. 12, Jan. 1, 2010 (Jan. 1, 2010), pp. 2790-2797.

An International Search Report and a Written Opinion both dated Mar. 18, 2016, which issued during the prosecution of Applicant's PCT/IL2015/051146.

An English translation of portions of an Office Action dated Jan. 4, 2015, which issued during the prosecution of Israel Patent Application No. 218247.

An Office Action dated Jun. 27, 2017, which issued during the prosecution of Japanese Patent Application No. 112337/2016.

An Office Action dated Jan. 19, 2016, which issued during the prosecution of Japanese Patent Application No. 2015-037378.

An International Search Report and a Written Opinion both dated May 30, 2018, which issued during the prosecution of Applicant's PCT/IL2018/050190.

(56)                References Cited

OTHER PUBLICATIONS

An Office Action together with the English Summary dated Oct. 25, 2019, which issued during the prosecution of Chinese Patent Application No. 201580074408.6.

Notice of Allowance dated Sep. 6, 2018, which issued during the prosecution of U.S. Appl. No. 15/852,293.

Notice of Allowance dated Sep. 23. 2019, which issued during the prosecution of U.S. Appl. No. 14/579,340.

An International Preliminary Report on Patentability dated Aug. 27. 2019, which issued during the prosecution of Applicant's PCT/IL2018/050190.

Dani, Raj K., et al. "Temperature-tunable iron oxide nanoparticles for remote-controlled drug release." AAPS PharmSciTech 15.4 (2014): 963-972.

O Eloy, Josimar, et al. "Stimuli-responsive nanoparticles for siRNA delivery." Current pharmaceutical design 21.29 (2015): 4131-4144.

Wang, Hui, et al. "Magnetic/NIR-thermally responsive hybrid nanogels for optical temperature sensing, tumor cell imaging and triggered drug release." Nanoscale 6.21 (2014): 13001-13011.

U.S. Appl. No. 62/461,902, filed Feb. 22, 2017.

An Office Action dated May 25, 2020, which issued during the prosecution of Canadian Patent Application No. 2,968,648.

An Office Action dated Jan. 31, 2020, which issued during the prosecution of Canadian Patent Application No. 2,968,648.

An Office Action together with the English Summary dated Aug. 3, 2020, which issued during the prosecution of Chinese Patent Application No. 201580074408.6.

An Office Action together with the English Summary dated Jan. 28, 2021, which issued during the prosecution of Chinese Patent Application No. 201580074408.6.

An Office Action dated Nov. 11, 2020, which issued during the prosecution of Indian Patent Application No. 201927036989.

Park, Sangphil, et al. "Magnetic nanoparticle-embedded PCM nanocapsules based on paraffin core and polyurea shell." Colloids and surfaces A: physicochemical and engineering aspects 450 (2014): 46-51.

Office Action dated May 7, 2021 issued in Chinese Application No. 201580074408.6.

Office Action dated Jun. 28, 2021 issued in Indian Application No. 201727021621.

Office Action dated Sep. 9, 2021 issued in Chinese Application No. 201880025727.1.

Notice of Re-examination in counterpart Chinese Patent Application No. 201880025727.1, dated Oct. 9, 2025.

Communication Article 94(3) EPC (rejection) in counterpart European Patent Application No. 18714616.2. dated Nov. 11, 2025.

Communication dated Dec. 16, 2025 from the United States Patent and Trademark Office in U.S. Appl. No. 19/350,504.

Translation of communication dated Mar. 12, 2026 in Chinese Application No. 201880025727.1.

* cited by examiner

PHASE-CHANGE NANOPARTICLE

CROSS REFERENCES TO RELATED APPLICATIONS

The present application is the US National Phase of PCT application IL2018/050190 to Hof, filed Feb. 20, 2018, which published as WO 2018/154566, and which claims priority from U.S. Provisional Patent Application 62/461,902 to Hof, entitled "Phase change nanoparticle," filed Feb. 22, 2017.

The present application is related to:

U.S. Ser. No. 15/478,849 to Hof (issued as U.S. Pat. No. 9,872,902), which is a continuation of PCT Application no. PCT/IL2015/051146 to Hof, filed Nov. 25, 2015 (published as WO 16/084082), which claims priority from U.S. Provisional Application 62/083,978 to Hof, entitled "Phase-change nanoparticle," filed Nov. 25, 2014; and U.S. Ser. No. 13/392,037 to Hof (issued as U.S. Pat. No. 9,572,695), which is the US National Phase of International Patent Application PCT/IL2010/000683 (published as WO 11/024,159) to Hof, entitled "Phase-change and shape-change materials, filed Aug. 22, 2010, which claims priority from:

U.S. Provisional Patent Application 61/275,068 to Hof, entitled "Phase change implant," filed Aug. 24, 2009;

U.S. Provisional Patent Application 61/275,071 to Hof, entitled "Shape and function change of implanted element," filed Aug. 24, 2009;

U.S. Provisional Patent Application 61/275,089 to Hof, entitled "Phase change materials for treating cancer," filed Aug. 24, 2009.

All of the above-referenced applications are incorporated herein by reference.

FIELD OF EMBODIMENTS OF THE INVENTION

Some applications of the present invention generally relate to medical apparatus. Specifically, some applications of the present invention relate to the use of phase-change materials.

BACKGROUND

Hyperthermia is a method of treating cancer, in which heat is applied to tissue of the cancer patient, in order to kill cancer cells within the tissue. Hyperthermia is typically used to treat cancer patients in combination with other therapies, such as radiotherapy and chemotherapy.

The Warburg effect describes the observation that most cancer cells predominantly produce energy by glycolysis followed by lactic acid fermentation, rather than by oxidation of pyruvate like most healthy cells. The Warburg effect results in cancer cells consuming more than 20 times the quantity of glucose to produce energy than do healthy cells, ceteris paribus.

When a solid material is heated until its melting point, the material undergoes a phase-change to its liquid state. During the phase-change, the material accumulates a certain amount of heat, which is called the latent heat of fusion, or the enthalpy change of fusion. The temperature of the material stays relatively constant when the phase change occurs.

SUMMARY OF EMBODIMENTS

In accordance with some applications of the present invention, a plurality of nanoparticles are administered to a subject who is suffering from cancer. The nanoparticles typically have the following characteristics:

(1) The nanoparticles preferentially bind to cancerous cells relative to healthy cells.

(2) The nanoparticles preferentially absorb energy transmitted toward the subject's body relative to absorption of the energy by tissue of the subject (3) The nanoparticles prevent healthy tissue surrounding the cancerous cells from being heated to a temperature that is greater than a given temperature.

Typically, each of the nanoparticles includes an inner core of a magnetic material. For some applications, the nanoparticle includes a plurality of inner cores of the magnetic material. The inner core is heated, via magnetic heating, e.g., using an alternating current radiofrequency-transmitting heating device. The magnetic material of the inner core has a Curie temperature, which is the maximum temperature to which the inner core can be heated. A phase-change material layer is disposed around the inner core, the phase-change material layer including a phase-change material. The phase-change material undergoes a phase-change at a given phase-change temperature. While undergoing the phase change, the temperature of the phase-change material remains constant at the phase-change temperature, due to the phase-change material absorbing latent heat of fusion.

Typically, the Curie temperature of the magnetic material (i.e., the maximum temperature to which the inner core can be raised) is greater than the phase-change temperature of the phase-change material, i.e., the phase-change temperature is lower than the Curie temperature. However, due to the relative thermal masses of the inner core and the phase-change-material layer in the nanoparticle, the phase-change material does not undergo a complete phase change, even if the inner core is subjected to continuous heating (e.g., via continuous transmission of RF energy) by the heating device. Therefore, tissue of the subject that surrounds the nanoparticle is heated to the phase-change temperature of the phase-change material, but is not exposed to a temperature that is greater than the phase-change temperature. Typically, heating the tissue of the subject that surrounds the nanoparticle to the phase-change temperature causes at least some of the cancerous cells to become heated, such that the heated cells become injured, or ruptured, leading to cell death.

For some applications, the nanoparticles are at least partially self-adjusting in shape, the nanoparticles being configured to be elongatable to an ellipsoid shape such as to pass through a gap in an anatomical barrier that has a size that is greater than a minimum threshold size, for example, in response to osmotic and/or hydrostatic pressure being exerted on the nanoparticles. It is noted that typically, the nanoparticles will not become elongated to a precise geometric ellipsoid shape, but will assume a generally ellipsoidal shape when maximally elongated.

There is therefore provided, in accordance with some applications of the present invention, apparatus for use with a subject, and for use with a heating device configured to heat at least a portion of the subject's body, the apparatus including:

a nanoparticle configured to be administered to the subject, the nanoparticle comprising:

at least one inner core that comprises a magnetic material having a Curie temperature;

a phase-change-material layer that surrounds the inner core and that comprises a phase-change material that is configured to absorb latent heat of fusion by undergoing a phase change selected from the group consisting of: solid to liquid, and gel to liquid, the phase-change occurring at a phase-change temperature that is lower than the Curie temperature;

an outer layer disposed around the phase-change-material layer, the outer layer comprising a plurality of nano-subparticles that are separated from one another, such as to form a segmented layer.

In some applications, the subject includes a subject suffering from cancer, the subject's body containing cancerous cells and non-cancerous cells, and the outer layer of the nanoparticle further includes a plurality of molecules of a substance that binds preferentially with cancerous cells relative to non-cancerous cells.

In some applications, the at least one inner core that includes a magnetic material having a Curie temperature includes a plurality of inner cores that include the magnetic material having a Curie temperature, and the phase-change material of the phase-change material layer surrounds each of the plurality of inner cores.

In some applications, the phase-change material is configured to undergo the selected phase change at a phase-change temperature of between 42 degrees Celsius and 60 degrees Celsius.

In some applications, the phase-change material is configured to undergo the selected phase change at a phase-change temperature of between 60 degrees Celsius and 80 degrees Celsius.

In some applications, the phase-change material is configured to prevent tissue that surrounds the nanoparticle from being heated to a temperature that is greater than the phase change temperature, by absorbing latent heat of fusion.

In some applications, the inner core is toxic, and the nano-subparticles are configured to shield the subject's body from toxicity of the inner core.

In some applications, the at least one inner core is composed of iron oxide ($Fe_3O_4$).

In some applications, the nano-subparticles include nano-spheres of at least one metal.

In some applications, the nano-subparticles include gold nano-subparticles.

In some applications, the nanoparticles are configured to be used with an alternating current radiofrequency heating device, and wherein the magnetic core is configured to be heated magnetically by the alternating current radiofrequency heating device.

In some applications, due to relative thermal masses of the inner core and the phase-change-material layer in the nanoparticle, the phase-change material does not undergo a complete phase change, even if the inner core is subjected to continuous heating by the heating device.

In some applications, the nanoparticle is elongatable into an ellipsoid, such that when the nanoparticle is maximally elongated:

each of the semi-axes defined by the ellipsoid is greater than 5 nm, and at least two of the semi axes of the ellipsoid are less than 30 nm.

In some applications, the nanoparticle is configured to become elongated in response to hydrostatic pressure within the subject's body.

In some applications, the nanoparticle is configured to become elongated in response to osmotic pressure within the subject's body.

In some applications, the nanoparticle is configured to be blocked from passing through a blood brain barrier of the subject, by being elongatable into the ellipsoid, such that even when the nanoparticle is maximally elongated, each of the semi-axes defined by the ellipsoid is greater than 5 nm.

In some applications, the nanoparticle is configured to be able to pass through a liver of the subject, by being elongatable into the ellipsoid, such that when the nanoparticle is maximally elongated at least two of the semi axes of the ellipsoid are less than 30 nm.

In some applications, the nanoparticle is configured to be able to pass through glands of the subject, by being elongatable into the ellipsoid, such that when the nanoparticle is maximally elongated at least two of the semi axes of the ellipsoid are less than 30 nm.

In some applications, the nanoparticle is configured to be able to pass through a mononuclear phagocyte system of the subject, by being elongatable into the ellipsoid, such that when the nanoparticle is maximally elongated at least two of the semi axes of the ellipsoid are less than 30 nm.

In some applications, the nanoparticle is configured to be able to pass through a spleen of the subject, by being elongatable into the ellipsoid, such that when the nanoparticle is maximally elongated at least two of the semi axes of the ellipsoid are less than 30 nm.

In some applications, the nanoparticle is elongatable into the ellipsoid, such that when the nanoparticle is maximally elongated each of the semi-axes defined by the ellipsoid is greater than 10 nm.

In some applications, the nanoparticle is elongatable into the ellipsoid, such that when the nanoparticle is maximally elongated at least two of the semi axes of the ellipsoid are less than 25 nm.

In some applications, the nanoparticle further includes a plurality of polymer chains disposed around the outer layer.

In some applications, the polymer chains include chains of a polymer selected from the group consisting of: polyetheramine, polypropylene, and polyethylene glycol.

In some applications, the polymer chains are configured to at least partially mask at least the outer layer from phagocytic cells of a mononuclear phagocyte system of the subject.

There is further provided, in accordance with some applications of the present invention, a method for use with a subject, the method including:

administering a plurality of nanoparticles to the subject, each of the nanoparticles including:

at least one inner core that comprises a magnetic material having a Curie temperature;

a phase-change-material layer that surrounds the inner core and that comprises a phase-change material that is configured to absorb latent heat of fusion by undergoing a phase change selected from the group consisting of: solid to liquid, and gel to liquid, the phase-change occurring at a phase-change temperature that is lower than the Curie temperature;

an outer layer disposed around the phase-change-material layer, the outer layer comprising a plurality of nano-subparticles that are separated from one another, such as to form a segmented layer.

There is further provided, in accordance with some applications of the present invention, a method including:

synthesizing a nanoparticle by:

providing at least one inner core that comprises a magnetic material having a Curie temperature;

binding a phase-change material layer around the inner core, the phase-change material layer including a phase-change material that is configured to absorb latent heat of fusion by undergoing a phase change selected from the group consisting of: solid to liquid, and gel to liquid, the phase-change occurring at a phase-change temperature that is lower than the Curie temperature; and binding an outer layer around the inner core, the outer layer including a plurality of nano-subparticles that are separated from one another, such as to form a segmented layer.

The present invention will be more fully understood from the following detailed description of embodiments thereof, taken together with the drawings, in which:

DETAILED DESCRIPTION OF EMBODIMENTS

Figure 1A:
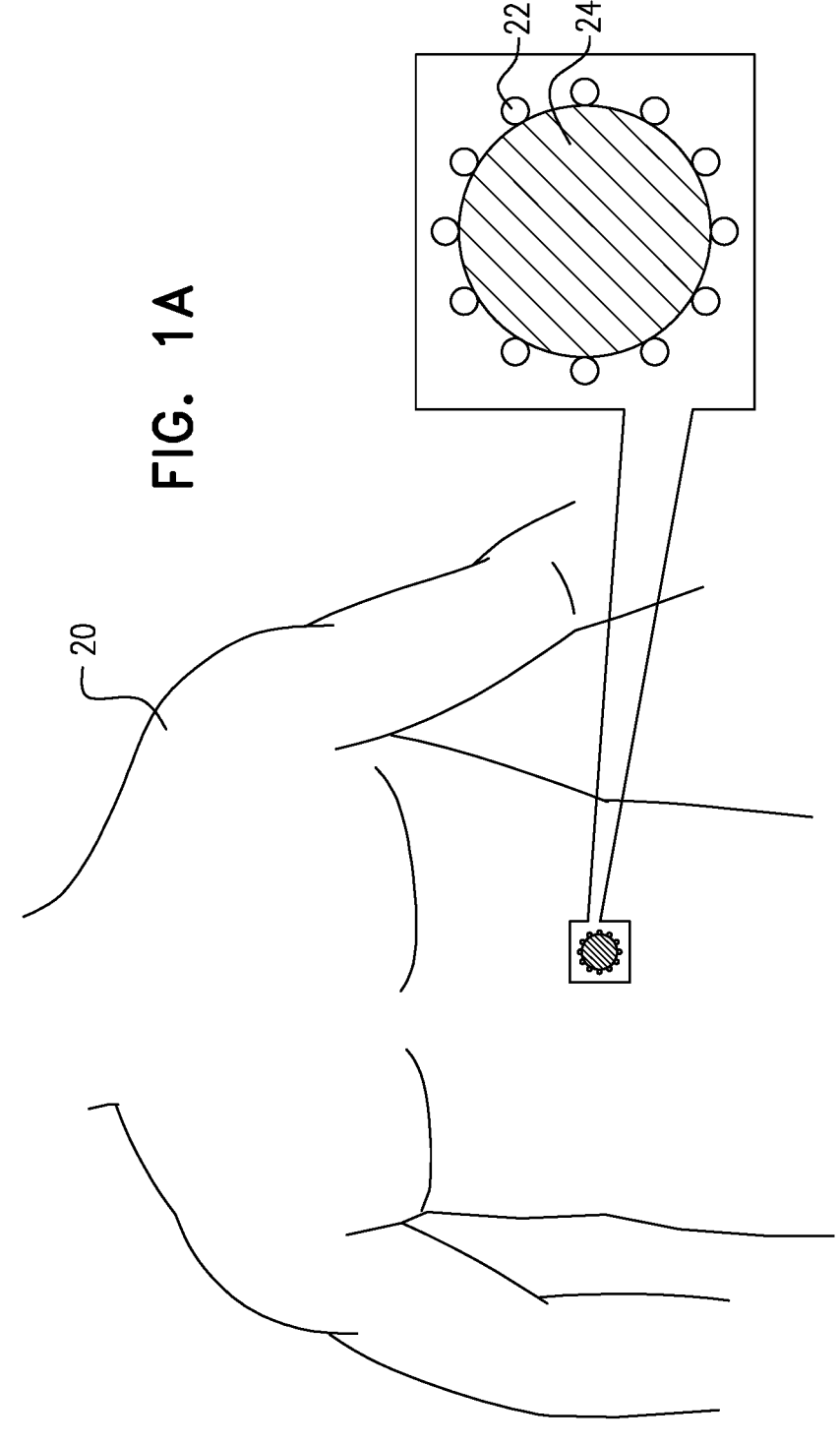
FIGS. 1A-B are schematic illustrations of a subject who is suffering from cancer, a plurality of nanoparticles having been administered to the subject and having become coupled to a tumor that contains cancerous cells, in accordance with some applications of the present invention.
Figure 1B:
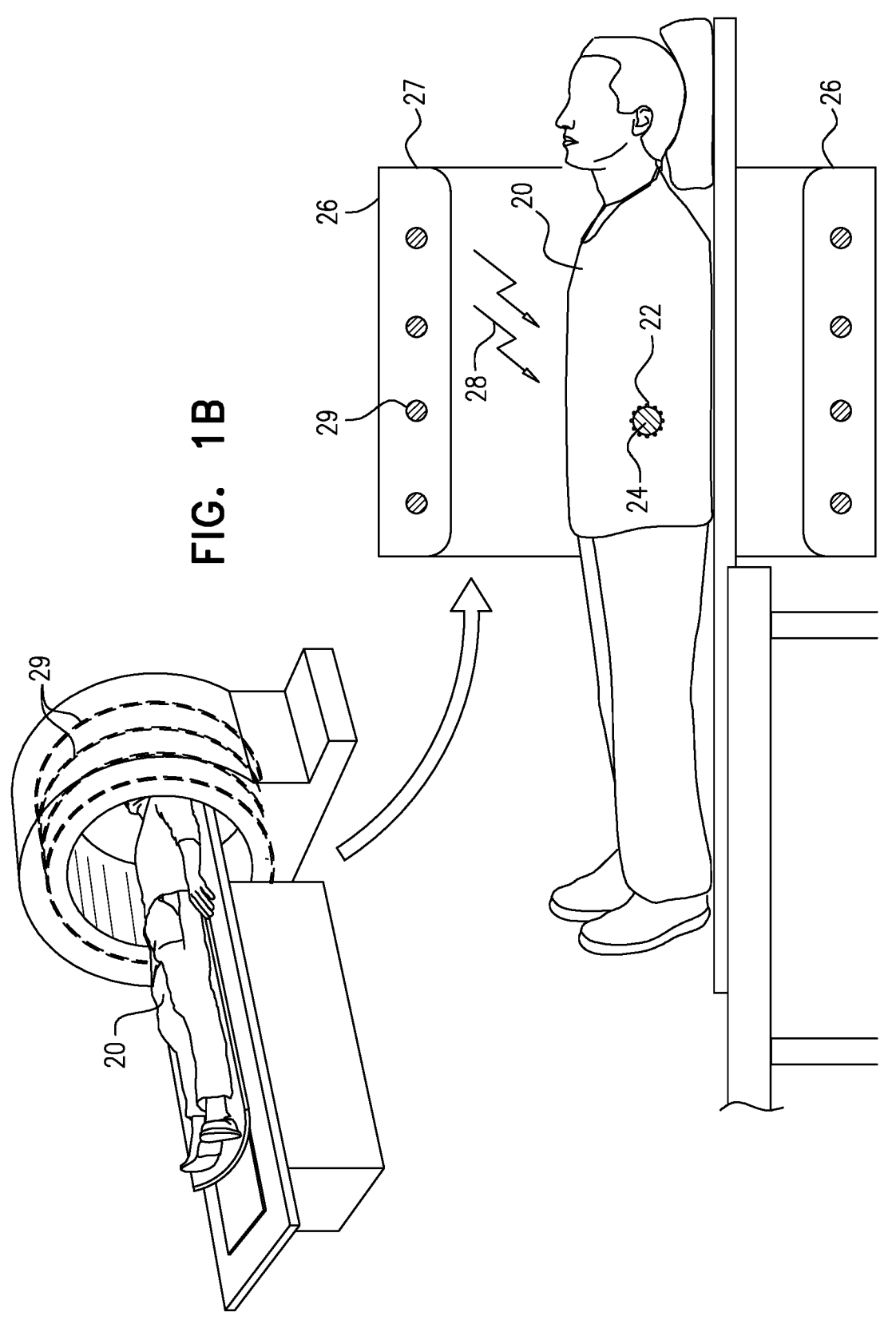

Reference is now made to FIGS. 1A-B, which are schematic illustrations of a subject 20 who is suffering from cancer, a plurality of nanoparticles 22 having been administered to the subject and having amassed at a tumor 24 that contains cancerous cells, in accordance with some applications of the present invention. As shown in FIG. 1B, a heating device 26 is typically used in conjunction with the administration of the nanoparticles to the subject. The heating device transmits energy (schematically illustrated by arrows 28) toward the subject's body, causing at least some of the cancerous cells to become heated, such that the heated cells become injured or ruptured, leading to cell death. The heating device acts as an energy transmission unit.

As described in detail hereinbelow, the nanoparticles typically have the following characteristics:

(1) The nanoparticles preferentially bind to cancerous cells relative to healthy cells.

(2) The nanoparticles preferentially absorb energy transmitted toward the subject's body relative to absorption of the energy by tissue of the subject (3) The nanoparticles prevent healthy tissue surrounding the cancerous cells from being heated to a temperature that is greater than a given temperature.

For some applications, the nanoparticles are used to heat a portion of a subject's body to a predefined temperature (in accordance with the techniques described herein) for a purpose other than to treat cancer. For some such applications, the nanoparticles are not configured to preferentially bind to cancerous cells relative to healthy cells.

For some applications, the nanoparticles are at least partially self-adjusting in shape, the nanoparticles being configured to be elongatable to an ellipsoid shape such as to pass through a gap in an anatomical barrier that has a size that is greater than a minimum threshold size, for example, in response to osmotic and/or hydrostatic pressure being exerted on the nanoparticles.

It is noted that typically, the nanoparticles will not become elongated to a precise geometric ellipsoid shape, but will assume a generally ellipsoidal shape when maximally elongated.

For some applications, the heating device 26 with which the nanoparticles are used is an RF-transmitter. Typically, alternating current (AC) heating is used, such that the nanoparticles are heated magnetically, as described in further detail hereinbelow. For some applications, the nanoparticles are heated via a different type of heating device, such as an ultrasound device, a laser device, etc. For some such applications, the inner core of the nanoparticles contains a different heat absorbing material, e.g., a heat absorbing material that is not magnetic. FIG. 1B shows the patient's body inside the heating device. As shown in the example that is shown in FIG. 1B, heating device (e.g., the RF-transmitter) may include a housing 27 that is shaped like an MRI scanner, such that the entire body of the subject, or an entire portion of the subject's body (e.g., the subject's torso, as shown) is disposed inside the housing. A coil 29 spirals around inside the housing and transmits energy in the general direction of the subject's body.

Alternatively or additionally, heating device 26 may include respective transmission and receiving electrodes (e.g., electrode plates) that are disposed on opposite sides of the subject's body (e.g., above and below the subject's body). For such applications, the heating device is configured to generate an electromagnetic field that passes through at least a portion of the subject's body, by transmitting electromagnetic energy from the transmission electrode to the receiving electrode.

Figure 2A:
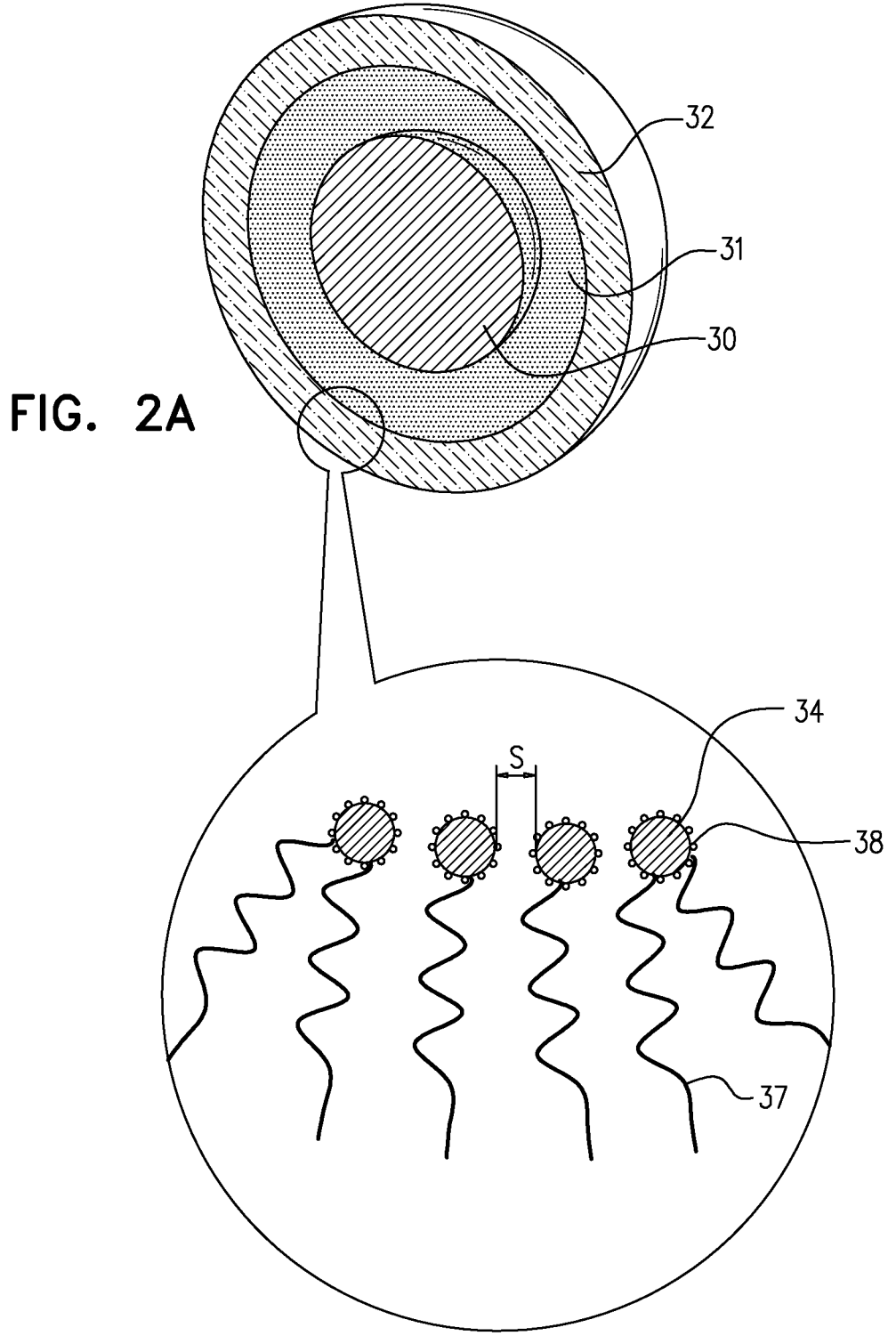
FIG. 2A is a schematic illustration of a three-dimensional cross-section of the nanoparticle, when, as shown for illustrative purposes, the nanoparticle is in a spherical shape, in accordance with some applications of the present invention.
Figure 2B:
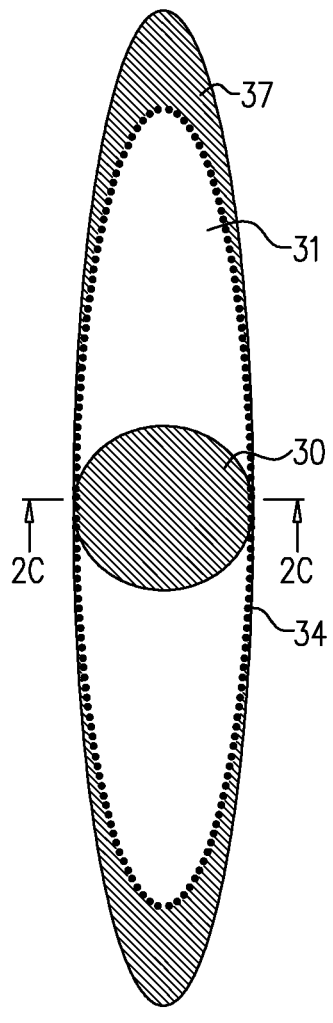
FIGS. 2B and 2C are schematic illustrations of respective two-dimensional cross-sections of the nanoparticle, while the nanoparticle is in an elongated configuration, in which the nanoparticle is shaped as an ellipsoid, in accordance with some applications of the present invention.
Figure 2C:
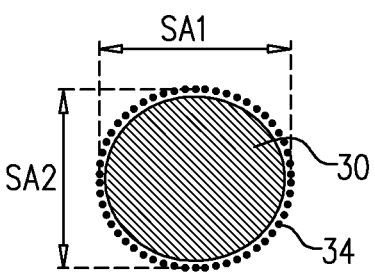

Reference is now made to FIG. 2A, which is a schematic illustration of a cross-section of nanoparticle 22, in accordance with some applications of the present invention. FIG. 2A shows a cross-section of the nanoparticle when the nanoparticle is shaped spherically, for illustrative purposes. Reference is also made to FIGS. 2B and 2C, which are schematic illustration of respective cross-sections of nanoparticle 22, when the nanoparticle is elongated and is shaped as an ellipsoid. It is noted that, for illustrative purposes, the relative dimensions of the respective components of the nanoparticle are not shown to scale in FIGS. 2A-C.

Figure 3:
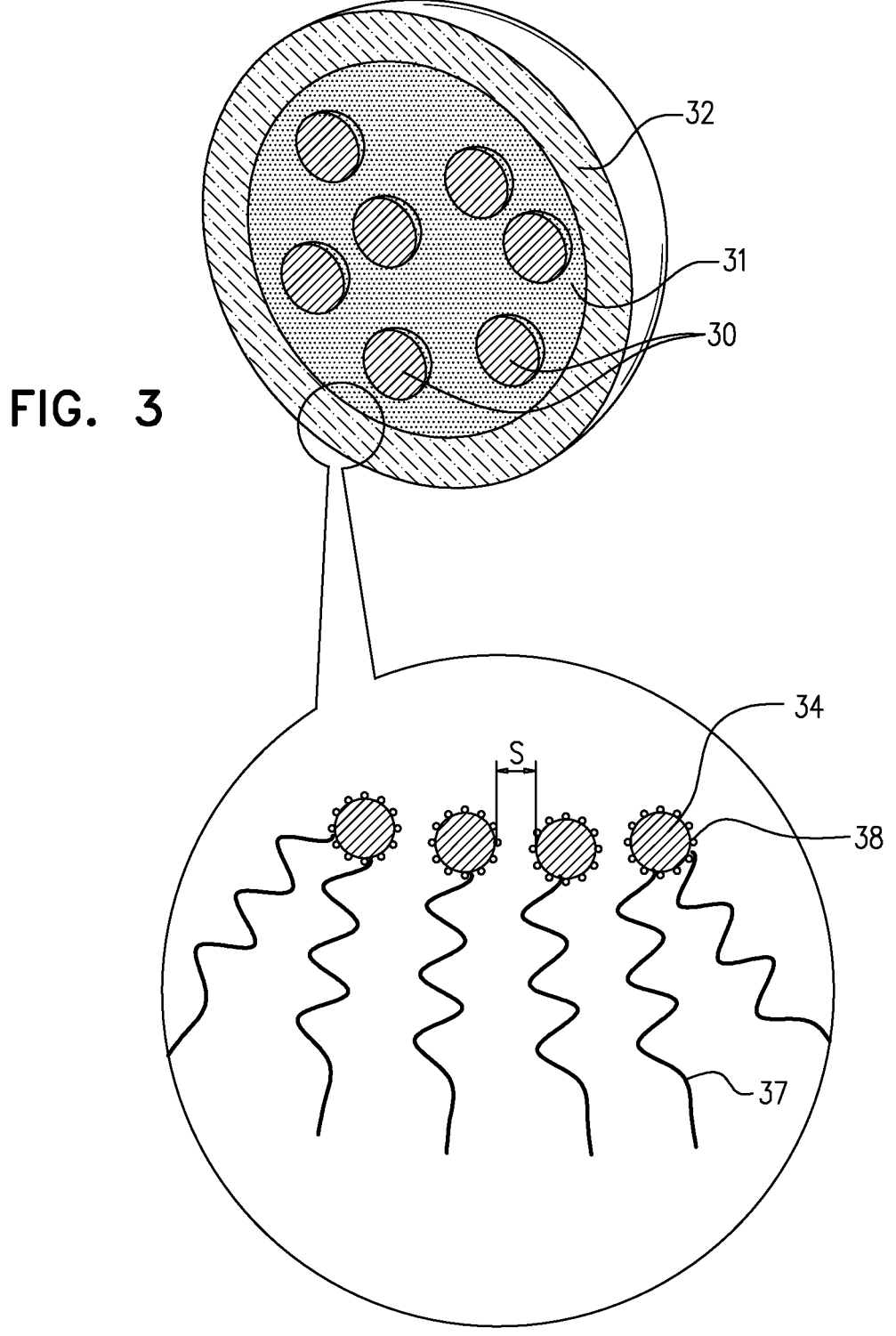
FIG. 3 is a schematic illustration of a three-dimensional cross-section of the nanoparticle, when, as shown for illustrative purposes, the nanoparticle is in a spherical shape, the nanoparticle including a plurality of inner cores, in accordance with some applications of the present invention.

As shown, nanoparticle 22 typically includes an inner core 30 that includes (e.g., is composed of) a magnetic material having a Curie temperature of more than 45 degrees Celsius (e.g., more than 100 degrees Celsius) and/or less than 1000 degrees Celsius (e.g., less than 800 degrees Celsius, or less than 500 degrees Celsius), e.g., between 45 degrees Celsius and 100 degrees Celsius, or between 100 degrees Celsius and 1000 degrees Celsius. For some applications, the inner core includes (e.g., is composed of) iron oxide ($Fe_3O_4$). A phase-change-material layer 31 is disposed around the inner core, the phase-change-material layer including a phase-change material, which is described in further detail hereinbelow. For some applications, each nanoparticle contains a plurality of inner cores, mutatis mutandis, e.g., as shown in FIG. 3. For some applications, the nanoparticles contain a heat absorbing material that is not magnetic. For such applications, heating device heats the inner core via non-magnetic heating, e.g., via ultrasound, laser, etc.

An outer layer 32 is disposed around the phase-change-material layer, the outer layer including a plurality of nano-subparticles 34 that typically include at least one metal. The term nano-subparticles is used to denote nanoparticles that comprise a portion of nanoparticle 22. Typically, the nano-subparticles are nano-spheres, although nano-subparticles having other shapes, such as cuboid, pyramid, or an irregular shape, are included within the scope of the invention. For some applications, the nano-subparticles are made of a non-metallic biocompatible substance, such as carbon. It is noted that the outer layer is typically not a continuous layer, but rather there are separations between each of the nano-subparticles and the nano-subparticles that are adjacent thereto, as described in further detail hereinbelow. Thus, outer layer 32 is segmented. For some applications, polymer chains 37 are disposed around the outside of outer layer 32, as shown.

As shown in the enlarged portion of FIG. 2A, for applications in which nanoparticle 22 is used to treat cancer, molecules 38 of a substance that binds preferentially with cancerous cells relative to non-cancerous cells are bound to nano-subparticles 34. Typically, glucose molecules, and/or molecules of a glucose analog or a glucose derivative (such as fluorodeoxyglucose and/or D-glucose), are used as the substance that binds preferentially with cancerous cells relative to non-cancerous cells. Typically, more than twenty times as many glucose (or glucose analog or glucose derivative) molecules may become coupled to the cancer cells as become coupled to the healthy cells. The preferential uptake of glucose molecules by cancer cells is based on the Warburg effect, described hereinabove in the Background, and as described in "Cancer's Molecular Sweet Tooth and the Warburg Effect," by Kim et al., Cancer Res 2006; 66: (18), Sep. 15, 2006, which is incorporated herein by reference. (The principle of cancer cells preferentially uptaking glucose molecules forms the basis of certain PET-CT imaging protocols.) For some applications, glucose (or a glucose analog or a glucose derivative) is used since glucose is absorbed even into anaerobic tissue, and cancerous tissue is typically anaerobic. Further typically, glucose, glucose analogs, and glucose derivatives bind with both solid tumors and hematological tumors. For some applications, a different type of molecule (e.g., an antibody, a drug, and/or a hormone) that preferentially binds with cancerous cells relative to non-cancerous cells is used.

For some applications, the nanoparticles are administered to the subject systemically (e.g., orally, and/or via intravenous injection), and the nanoparticles are configured to preferentially bind with the cancer cells, by virtue of the fact that the nanoparticle includes the substance that binds preferentially with cancerous cells relative to non-cancerous cells. In this manner, the nanoparticles typically amass in the vicinity of a cancerous tumor (e.g., tumor 24, shown in FIG. 1A), and bind with cells of the tumor. For some applications, even in the event that the cancer has metastasized the nanoparticles amass around and bind with metastasized cancer cells.

For some applications, the nanoparticles are used to heat a portion of a subject's body to a predefined temperature (in accordance with the techniques described herein) for a purpose other than to treat cancer. For some such applications, the nanoparticles are not configured to preferentially bind to cancerous cells relative to healthy cells. Typically, for such applications, nanoparticle 22 does not include molecules 38 of the substance that binds preferentially with cancerous cells relative to non-cancerous cells.

Typically, outer layer 32 includes a plurality of nano-subparticles 34 of at least one metal. Typically, nano-subparticles 34 include a noble metal such as ruthenium, rhodium, palladium, silver, osmium, iridium, platinum, and/or gold. For some applications, nano-subparticle 34 is a paramagnetic gold superatom nano-sphere. For some applications, an alloy that includes a mixture of two or more metals, or a metal and a nonmetal, is used for nano-subparticles 34. For some applications, nano-subparticle 34 is a non-metallic biocompatible substance, such as carbon. As described hereinabove, for some applications, inner core(s) 30 includes iron oxide, which is toxic. Typically, the metal that is used for the nano-subparticles is selected so as to shield the subject's body from any toxicity that is present in the inner core. For example, gold or carbon nano-subparticles may be used. For some applications, polymer chains 37 provide additional shielding, as described in further detail hereinbelow.

As noted hereinabove, outer layer 32 is typically not a continuous layer, but rather there are separations between each of the nano-subparticles and the nano-subparticles that are adjacent thereto, such that layer 32 is segmented. Typically, a diameter of each of the nano-subparticles is greater than 1 nm (e.g., greater than 3 nm), and/or less than 10 nm (e.g., less than 7 nm), e.g., between 1 and 10 nm, or between 3 nm and 7 nm. Further typically, when nanoparticle 22 is in its spherical configuration (FIG. 2A), a separation S between each of the nano-subparticles and an adjacent nano-subparticle is greater than 0.3 nm (e.g., greater than 0.5 nm), and/or less than 2 nm (e.g., less than 1.5 nm), e.g., between 0.3 nm and 2 nm, or between 0.5 nm and 1.5 nm. The separation between the nano-subparticles allows the nano-subparticles to move with respect to each other, which contributes to the nanoparticle having the property of being self-adjusting in shape. By contrast, if outer layer 32 were to be formed as a continuous layer of metal, the outer layer would be relatively rigid. The separation between the nano-subparticles is typically not greater than the maximum separation described herein, in order to prevent phagocytic cells of the subject's mononuclear phagocyte system (i.e., the subject's reticuloendothelial system) from penetrating outer layer 32, and in order to shield the subject's body from any toxicity that is present in the inner core, as described hereinabove.

As described hereinabove, heating device 26 is typically used to transmit energy (e.g., RF energy) toward the subject's body. Typically, alternating current (AC) heating is used, such that inner core 30 is heated magnetically. As described hereinabove, typically, inner core 30 includes (e.g., is composed of) a magnetic material having a Curie temperature of more than 45 degrees Celsius (e.g., more than 100 degrees Celsius) and/or less than 1000 degrees Celsius (e.g., less than 800 degrees Celsius, or less than 500 degrees Celsius), e.g., between 45 degrees Celsius and 100 degrees Celsius, or between 100 degrees Celsius and 1000 degrees Celsius. Upon reaching its Curie temperature, the magnetic material loses its magnetic properties and is no longer heated. Therefore, the maximum temperature to which the inner core can be heated is the Curie temperature of the material from which the inner core is made.

Nanoparticle 22 typically includes phase-change-material layer 31, which includes a phase-change material. Typically, upon being heated to a phase-change temperature of the phase-change material, the phase-change material is configured to undergo a change of phase from solid to liquid, solid to gel, or gel to liquid. Typically, by virtue of the inner core being heated, as described hereinabove, the phase change material is heated to its phase-change temperature. Typically, due to heat being absorbed by the phase-change material as latent heat of fusion, once the phase-change material has been heated to the phase-change temperature, the temperature of the phase-change material remains substantially constant at the phase-change temperature and does not rise to a temperature that is greater than the phase-change temperature. Therefore, outer layer 32 and the tissue that surrounds nanoparticle 22 are heated to the phase-change temperature of the phase-change material. Typically, the phase-change material has a phase-change temperature of more than 42 degrees Celsius and/or less than 90 degrees Celsius (e.g., less than 60 degrees Celsius), e.g., between 42 degrees Celsius and 90 degrees Celsius or between 50 degrees Celsius and 60 degrees Celsius.

Typically, the Curie temperature of the magnetic material (i.e., the maximum temperature to which the inner core can be raised) is greater than the phase-change temperature of the phase-change material, i.e., the phase-change temperature is lower than the Curie temperature. However, due to the relative thermal masses of the inner core and the phase-change-material layer in the nanoparticle, the phase-change material does not undergo a complete phase change, even if the inner core is subjected to continuous heating (e.g., via continuous transmission of RF energy) by the heating device. Therefore, tissue of the subject that surrounds the nanoparticle is heated to the phase-change temperature of cancer cells, by virtue of the fact that the nanoparticle includes the substance that binds preferentially with cancerous cells relative to non-cancerous cells. In this manner, the nanoparticles typically amass in the vicinity of a cancerous tumor (e.g., tumor 24, shown in FIG. 1A), and bind with cells of the tumor. As an additional safety mechanism for reducing damage to healthy tissue, typically, the phase-change material is chosen such that the phase-change temperature is a temperature at which the cancer cells will be substantially damaged (e.g., injured or ruptured) but such that the healthy cells in the surrounding tissue will not be substantially damaged. (It is noted that typically some healthy cells may be at least partially damaged.) Since the phase-change material maintains the temperature of the outer layer of the nanoparticles at the phase-change temperature, the heating of the nanoparticles is such as to damage the cancer cells in the vicinity of the nanoparticles but not to substantially damage the healthy cells in the vicinity.

For some applications, the effect of the heating of the nanoparticles on the cancer is in accordance with Table 1, which appears in an article by Thomsen, entitled "Pathologic analysis of photothermal and photomechanical effects of laser-tissue interactions" (Photochem Photobiol. 1991 June; 53(6): 825-35), which is incorporated herein by reference:

TABLE 1

| Histopathological effect of heating on cells | | | |
|---|---|---|---|
| Thermal damage mechanism | Temperature of onset: range (degrees Celsius) | Heating times | Histopathology effect |
| Low-temperature damage accumulation processes | 40-45 | Hours | Reversible cell injury: heat inactivation of enzymes; metabolic acceleration |
| | Low 40+ | Hours to minutes | Edema and hyperemia |
| | 43-45+ | Hours | Cell death: deactivation of enzymes |
| | Unknown | Unknown | Cell shrinkage and hyperchromasia |
| | 43+ | Minutes | Birefringence loss in frozen and thawed myocardium |
| | 45+ | Minutes to seconds | Thermal denaturization of structural proteins in fresh tissue |
| | Unknown | Unknown | Cell membrane rupture |
| | 50-90 | Minutes to seconds | Hyalinization of collagen |
| | 54-78 | 3.6 to 0.4 seconds | Birefringence loss in laser irradiated fresh myocardium |
| | 55-95+ | Minutes | Birefringence changes in collagen |
| Water dominated processes | 100 | Seconds | Extracellular vacuole formation. Rupture of vacuoles, "popcorn" effect |
| | 100-200 | Seconds to milliseconds | Tissue ablation by explosive fragmentation |
| | Over 200 | Seconds to picoseconds | Tissue ablation | the phase-change material, but is not exposed to a temperature that is greater than the phase-change temperature.

As described hereinabove, for some applications, nanoparticles 22 are configured to preferentially bind with the For some applications, one or more of the phase-change materials that appear in Table 2 and/or in Table 3 (which are extracted from Zalba et al., Applied Thermal Engineering, 23(3), February 2003, pp. 251-283) is used as the phase-change material of phase-change-material layer 31.

TABLE 2

Melting temperatures of paraffin particles

| Compound | Melting temperature (degrees Celsius) | Heat of fusion (Kj/Kg) |
|---|---|---|
| Paraffin C16-C28 | 42-44 | 189 |
| Paraffin C20-C33 | 48-50 | 189 |
| Paraffin C22-C45 | 58-60 | 189 |
| Paraffin wax | 64 | 173.6 |
| Paraffin C28-C50 | 66-68 | 189 |
| Paraffin RT40 | 43 | 181 |
| Paraffin RT50 | 54 | 195 |
| Paraffin RT65 | 64 | 207 |
| Paraffin RT80 | 79 | 209 |
| Paraffin RT90 | 90 | 197 |
| Paraffin RT110 | 112 | 213 |

TABLE 3

Melting temperature of organic phase-change materials:

| Compound | Melting Temperature (degrees Celsius) | Heat of Fusion (Kj/Kg) |
|---|---|---|
| Paraffin C14 | 4.5 | 165 |
| Paraffin C15-C16 | 8 | 153 |
| Polyglycol E400 | 8 | 99.6 |
| Dimethyl-sulfoxide (DMS) | 16.5 | 85.7 |
| Paraffin C16-C18 | 20-22 | 152 |
| Polyglycol E600 | 22 | 189 |
| Paraffin C13-C24 | 22-24 | 189 |
| 1-Dodecanol | 26 | 200 |
| Paraffin C18 | 28 | 244 |
| 1-Tetradecanol | 26 | 200 |
| Paraffin C16-C28 | 42-44 | 189 |
| Paraffin C20-C33 | 48-50 | 189 |
| Paraffin C22-C45 | 58-60 | 189 |
| Paraffin Wax | 64 | 173.6 |
| Polyglycol E6000 | 66 | 190 |
| Paraffin C28-C30 | 66-68 | 189 |
| Biphenyl | 71 | 119.2 |
| Propionamide | 79 | 168.2 |
| Naphthalene | 80 | 147.7 |
| Erythritol | 118 | 339.8 |
| HDPE | 100-150 | 200 |
| Trans-1,4-polybutadiene (TPB) | 145 | 144 |

For some applications, one or more of the following organic phase-change materials is used for the phase-change material of phase-change-material layer 31: crude oil, paraffin produced by the Fischer-Tropsch process, and an organic material having saturated, unsaturated, straight, or branched carbon chain particles. The phase-change material may include, for example, trilaurin, trimyristin, tripalmitin, tristearin, and/or any suitable type of paraffin or paraffin wax.

For some applications, an organic phase-change material is used in phase-change-material layer 31. For example, paraffin and/or fatty acid particles may be used. For some applications, an organic material is used in inner core 30 because the organic phase-change material freezes without substantial super cooling, is able to melt congruently, has self-nucleating properties, does not segregate, is chemically stable, has a high heat of fusion, and/or for a different reason. For some applications, one or more of the following phase-change materials is used in inner core 30: Octadecane (CAS Number 593-45-3), Lauric acid (CAS No: 143-07-7), Myristic acid (CAS No: 544-63-8), Palmitic acid (CAS No: 57-10-3), Heptadecanoic acid (CAS No: 506-12-7), Stearic acid (CAS No: 57-11-4), Arachidic acid (CAS No: 506-30-9), Behenic acid (Cas No: 112-85-6) Trimethylolethane (CAS No: 77-85-0), Stearamine (Octadecylamine) (Sigma-74750), Cetylamine (Hexadecylamine) (Sigma-445312).

In accordance with respective applications of the invention, selection criteria for selecting the phase-change material for use in phase-change-material layer 31 include thermodynamic, kinetic, and chemical properties of the phase-change material. For some applications, the phase-change material is selected to have given thermodynamic properties, such as a melting temperature in the desired operating temperature range, a high latent heat of fusion per unit volume, high specific heat, high density, high thermal conductivity, small volume changes on phase transformation, small vapor pressure at operating temperatures, and/or congruent melting. For some applications, the phase-change material is selected to have given kinetic properties, such as a high nucleation rate, and/or a high rate of crystal growth. For some applications, the phase-change material is selected to have given chemical properties, such as chemical stability, reversibility of the phase-change cycle without degradation of the particles after a large number of phase-change cycles, non-corrosiveness, and/or non-toxicity.

For some applications, the phase-change material has relatively low thermal conductivity, and is arranged to have a large surface area to overcome the low thermal conductivity and increase the flow of heat into the phase-change material.

Since nanoparticles 22 typically amass in the vicinity of cancer cells and bind with the cancer cells, and the inner core preferentially absorbs the energy that is transmitted toward the subject, the cancer cells are preferentially heated relative to healthy cells of the subject. Due to the nanoparticles 22 amassing in the vicinity of cancer cells and binding with the cancer cells, the average heat flux density (i.e., the heat rate per unit area) at the cancer cells within the region of the subject's body that is heated by the heating device is typically substantially greater (e.g., more than twice as great, more than 5 times greater, more than 10 times greater, and/or more than 20 times greater) than that of the average heat flux density at the healthy cells within the region that is heated by the heating device. As a result, the heating of the subject's body (or the portion thereof) by the heating device is typically such as to damage the cancer cells in the subject's body (or in the heated portion) but not to substantially damage the healthy cells therein.

As described hereinabove, and as shown in the transition from FIG. 2A to FIG. 2B, typically, nanoparticle 22 is at least partially self-adjusting in shape, the nanoparticles being configured to be elongatable to a generally ellipsoid shape (e.g., a tri-axial ellipsoid shape, or a prolate or oblate ellipsoid of revolution shape). It is noted that typically, the nanoparticle will not become elongated to a precise geometric ellipsoid shape, but will assume a generally ellipsoidal shape when maximally elongated.

Typically, in order for a cancer treatment as described herein to be effective, nanoparticles 22 need to have a certain minimum volume, for at least one of the following reasons:

(1) Tumor cells tend not to bind with particles that are below a given volume.

(2) A minimum volume of the material from which inner core 30 is made is required such as to facilitate preferential absorption of energy by nanoparticles 22. In this manner, the average heat flux density at the cancer cells within the region of the subject's body that is heated by the heating device is substantially greater than that of the average heat flux density at the healthy cells within the region that is heated by the heating device, as described hereinabove.

(3) It is required that the phase-change-material layer 31 have a given minimum volume, in order for the phase-change material to effectively absorb heat as latent heat of fusion, such as to prevent the temperature of the nanoparticle from rising above the phase-change temperature.

Typically, inner core 30 of the magnetic material has a volume of at least 0.5 nm^3, e.g., at least 60 nm^3, or at least 1,500 nm^3. For some applications, inner core 30 of the phase-change material has a volume of less than 70,000 nm^3, e.g., less than 40,000 nm^3, or less than 15,000 nm^3. For example, inner core 30 may have a volume of 0.5-70, 000 nm^3, e.g., 60-40,000 nm^3, or 1,500-15,000 nm^3. As noted hereinabove, for some applications, the nanoparticle includes a plurality of inner cores (e.g. a plurality of iron oxide nano-subparticles), e.g., as shown in FIG. 3. In such cases, the aforementioned volumes of the inner core apply to the total volume of all of the inner cores within the nanoparticle.

For some applications, when inner core 30 is shaped spherically (as shown in FIG. 2A), inner core 30 of the magnetic material has a diameter of at least 1 nm, e.g., at least 5 nm, at least 15 nm, or at least 25 nm. For some applications, when inner core 30 is shaped spherically, inner core 30 of the magnetic material has a diameter of less than 50 nm, e.g., less than 40 nm, or less than 30 nm. For example, when inner core 30 is shaped spherically, inner core 30 may have a diameter of 1-50 nm, 5-40 nm, or 15-30 nm.

Typically, phase-change-material layer 31 of the phase-change material has a volume of at least 200 nm^3, e.g., more than 2000 nm^3. For some applications, phase-change-material layer 31 of the phase-change material has a volume of less than 15,000 nm^3, e.g., less than 8000 nm^3. For example, phase-change-material layer 31 of the phase-change material may have a volume of 200-15,000 nm^3, e.g., 2000-8000 nm^3. Typically, the thickness of the phase-change material layer (which surrounds the inner core) is more than 1 nm, and/or less than 10 nm, e.g., 1-10 nm.

As described hereinabove, typically, the diameter of each of nano-subparticles 34 is greater than 1 nm (e.g., greater than 3 nm), and/or less than 10 nm (e.g., less than 7 nm), e.g., between 1 and 10 nm, or between 3 nm and 7 nm. The length of each of polymer chains 37, when the chain is maximally straightened, is typically greater than 1 nm (e.g., greater than 1.5 nm), and/or less than 4 nm (e.g. less than 3 nm), e.g., 1-4 nm, or 1.5-3 nm. The length of each of polymer chains 37, when the chain is maximally straightened, is typically greater than 2 nm (e.g., greater than 4 nm), and/or less than 10 nm (e.g. less than 8 nm), e.g., 2-10 nm, or 4-8 nm.

Nanoparticle 22 typically has a volume of at least 1000 nm^3, e.g., more than 10,000 nm^3. Further typically, in its spherical configuration (shown in FIG. 2A), the nanoparticle has diameter volume of less than 400,000 nm^3, e.g., less than 100,000 nm^3. For some applications, the nanoparticle has a volume of 1000-400,000 nm^3, e.g., 10,000-100,000 nm^3.

When it is shaped spherically (as shown in FIG. 2A), nanoparticle 22 typically has a diameter of at least 15 nm, e.g., at least 30 nm. Further typically, in its spherical shape, the nanoparticle has a diameter of less than 90 nm, e.g., less than 70 nm. For some applications, in its spherical shape, the nanoparticle has a diameter of 15-90 nm, or 30-70 nm.

It is noted that, solely for illustrative purposes, nanoparticle 22 is shown in FIG. 2A in a spherical configuration, and the dimensions of nanoparticle 22 are provided hereinabove, for when the nanoparticle is shaped spherically. However, nanoparticle 22 does not necessarily assume a spherical shape when in the subject's blood stream, even if the nanoparticle is not being subjected to osmotic, hydrostatic, and/or any other pressure inside the body. Rather, the nanoparticle may assume, for example, a tear shape, a bobble shape, an ellipsoid shape, and/or may be amorphous. However, nanoparticle 22 does have a substantially fixed volume, as provided hereinabove. Furthermore, the nanoparticle is typically configured to be at least partially self-adjusting in shape, such that the nanoparticle is able to pass through an anatomical barrier having a size that is greater than a threshold minimum size, for example, in response to hydrostatic and/or osmotic pressure being exerted on the nanoparticle, as described in further detail hereinbelow.

Typically, the following features of nanoparticle 22 contribute to the nanoparticle being self-adjusting in shape:

1) Phase-change-material layer 31 is made of a phase change material, such as paraffin, which is amorphous.
2) Nano-subparticles 34 are disposed at a separation from one another, such that each of the nano-subparticles is able to move with respect to the other nano-subparticles.
3) Polymer chains 37 are deformable and may change shape, for example, from a straight line to a coiled configuration.

Typically, nanoparticles 22 are administered to the subject systemically (e.g., orally, and/or intravenously). For some applications, in order to prevent the liver, spleen, glands, and/or any portion of the subject's mononuclear phagocyte system (i.e., the subject's reticuloendothelial system), from filtering the nanoparticles out of the subject's blood, the nanoparticles are configured to elongate (as shown schematically in FIGS. 2B and 2C) into a generally ellipsoid shape, such that at least two of the semi-axes of the ellipsoid have a diameter of less than 30 nm, e.g., less than 25 nm. For example, as shown in FIG. 2C, one of the semi axes of the nanoparticle SA1 is typically less than 30 nm, e.g., less than 25 nm, and a second one of the semi axes of the nanoparticle SA2 is typically less than 30 nm, e.g., less than 25 nm. As noted above, typically, the nanoparticle will not become elongated to a precise geometric ellipsoid shape, but will assume a generally ellipsoidal shape when maximally elongated.

For some applications, even in its maximally elongated configuration (i.e., in the configuration in which the nanoparticle is elongated into a generally ellipsoidal shape, but cannot be any further elongated), nanoparticle 22 is configured such that each of the semi axes of the ellipsoid is greater than 5 nm, e.g., greater than 10 nm. For example, as shown in FIG. 2C, both semi axes SA1 and SA2 are greater than 5 nm, e.g., greater than 10 nm. For some applications, in this manner, the nanoparticle is prevented from traversing the blood brain barrier. As described hereinabove, for some applications, outer layer 32 includes molecules of a substance that binds preferentially with cancerous cells relative to non-cancerous cells. Some of the substances that preferentially bind with cancer cells (e.g., antibodies, glucose, and glucose analogs or derivatives (such as fluorodeoxyglucose and/or D-glucose)) also have preferential uptake by the brain relative to the rest of the body. Therefore, nanoparticle 22 is typically configured such that even in its maximally elongated configuration, each of the semi axes of the ellipsoid is greater than 5 nm, e.g., greater than 10 nm, in order to prevent the nanoparticle from being able to traverse the blood brain barrier.

As described hereinabove, typically, polymer chains 37 are disposed at the outside of outer layer 32. Typically, a polyetheramine, e.g., a Jeffamine÷ polyetheramine, such as polyethylene glycol (PEG) or polypropylene, is used in polymer chains 37. Polymer chains 37 at least partially mask other components of nanoparticle 22 from phagocytic cells of the subject's mononuclear phagocyte system (i.e., the subject's reticuloendothelial system), thereby preventing the nanoparticle from being broken down by the phagocytic cells. Even if the polymer chains are broken down, nano-subparticles 34 shield the subject's body from any toxicity that is present in the inner core. For example, gold nano-subparticles may be used.

For some applications, the methods described herein are applied to the subject while imaging the subject, for example, using CT, sonic, ultrasonic, and/or MRI imaging protocols. For some applications, the substance is administered to the subject, and the subject's body (or a region thereof) is irradiated with the energy that is preferentially absorbed by the clusters, as described herein. While the subject's body is irradiated, the subject's body is imaged using a heat-sensitive imaging protocol (for example, using MRI) to detect which regions of the subject's body (including cancer cells) have been heated.

Reference is now made to FIG. 3, which is a schematic illustration of nanoparticle 22, the nanoparticle including a plurality of inner cores 30, each of which is surrounded by phase-change material of phase-change material layer 31, in accordance with some applications of the present invention. As described hereinabove, for some applications, rather than having a single inner core, nanoparticle 22 includes a plurality of cores, as shown. Typically, the cores have similar properties to those described hereinabove. Typically, each of the inner cores includes a magnetic material having a Curie temperature of more than 45 degrees Celsius (e.g., more than 100 degrees Celsius) and/or less than 1000 degrees Celsius (e.g., less than 800 degrees Celsius, or less than 500 degrees Celsius), e.g., between 45 degrees Celsius and 100 degrees Celsius, or between 100 degrees Celsius and 1000 degrees Celsius. For some applications, each of the inner cores includes (e.g., is composed of) iron oxide ($Fe_3O_4$).

As described hereinabove, for some applications, the nanoparticles are used to heat a portion of a subject's body to a predefined temperature (in accordance with the techniques described herein) for a purpose other than to treat cancer. For example, the nanoparticles could be used for destroying pathogens within the body such as viruses, bacteria, etc. For some such applications, the nanoparticles are not configured to preferentially bind to cancerous cells relative to healthy cells. For some such applications, the nanoparticles include antibodies on outer layer 32, the antibodies being configured to preferentially being to a given type of pathogen relative to healthy human cells.

For some applications, the apparatus and methods described herein are performed in combination with apparatus and methods described in U.S. Pat. No. 9,572,695 to Hof and/or in U.S. Pat. No. 9,872,902 to Hof, both of which are incorporated herein by reference.

There is therefore provided, in accordance with some applications of the present invention, the following inventive concepts:

Inventive concept 1. Apparatus for use with a subject, and for use with a heating device configured to heat at least a portion of the subject's body, the apparatus comprising:

a nanoparticle configured to be administered to the subject, the nanoparticle comprising:

at least one inner core that comprises a magnetic material that is configured to be heated by the heating device;

a phase-change-material layer that surrounds the inner core and that comprises a phase-change material that is configured to absorb latent heat of fusion by undergoing a phase change selected from the group consisting of: solid to liquid, and gel to liquid, the phase-change occurring at a phase-change temperature that is lower than the Curie temperature of the inner core, relative thermal masses of the inner core and the phase-change-material layer in the nanoparticle being such that the phase-change material does not undergo a complete phase change, even if the inner core is subjected to continuous heating by the heating device;

an outer layer disposed around the phase-change-material layer, the outer layer comprising a plurality of nano-subparticles that are separated from one another, such as to form a segmented layer.

Inventive concept 2. The apparatus according to inventive concept 1, wherein the at least one inner core that comprises a magnetic material having a Curie temperature comprises a plurality of inner cores that comprise the magnetic material having a Curie temperature, and wherein the phase-change material of the phase-change material layer surrounds each of the plurality of inner cores.

Inventive concept 3. The apparatus according to inventive concept 1, wherein the subject includes a subject suffering from cancer, the subject's body containing cancerous cells and non-cancerous cells, and wherein the outer layer of the nanoparticle further comprises a plurality of molecules of a substance that binds preferentially with cancerous cells relative to non-cancerous cells.

Inventive concept 4. The apparatus according to inventive concept 1, wherein the phase-change material is configured to prevent tissue that surrounds the nanoparticle from being heated to a temperature that is greater than the phase change temperature, by absorbing latent heat of fusion.

Inventive concept 5. The apparatus according to inventive concept 1, wherein the inner core is toxic, and wherein the nano-subparticles are configured to shield the subject's body from toxicity of the inner core.

Inventive concept 6. The apparatus according to inventive concept 1, wherein the at least one inner core is composed of iron oxide ($Fe_3O_4$).

Inventive concept 7. The apparatus according to inventive concept 1, wherein the nanoparticles are configured to be used with an alternating current radiofrequency heating device, and wherein the at least one magnetic core is configured to be heated magnetically by the alternating current radiofrequency heating device.

Inventive concept 8. The apparatus according to inventive concept 1, wherein the nano-subparticles comprise gold nano-subparticles.

Inventive concept 9. The apparatus according to inventive concept 1, wherein the nano-subparticles comprise metal nano-spheres.

Inventive concept 10. The apparatus according to any one of inventive concepts 1-9, wherein the nanoparticle is elongatable into an ellipsoid, such that when the nanoparticle is maximally elongated:

each of the semi-axes defined by the ellipsoid is greater than 5 nm, and at least two of the semi axes of the ellipsoid are less than 30 nm.

Inventive concept 11. The apparatus according to any one of inventive concepts 1-9, wherein the nanoparticle further comprises a plurality of polymer chains disposed around the outer layer.

Inventive concept 12. A method for use with a subject, and for use with a heating device configured to heat at least a portion of the subject's body, the method comprising:

administering a plurality of nanoparticles to the subject, each of the nanoparticles including:

an inner core that comprises a magnetic material;

a phase-change-material layer that surrounds the inner core and that comprises a phase-change material that is configured to absorb latent heat of fusion by undergoing a phase change selected from the group consisting of: solid to liquid, and gel to liquid, the phase-change occurring at a phase-change temperature that is lower than the Curie temperature of the inner core, relative thermal masses of the inner core and the phase-change-material layer in the nanoparticle being such that the phase-change material does not undergo a complete phase change, even if the inner core is subjected to continuous heating by the heating device;

an outer layer disposed around the phase-change-material layer, the outer layer comprising a plurality of nano-subparticles of at least one metal.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A nanoparticle for use with an alternating current radiofrequency (RF) heating device, the nanoparticle configured to be intravenously administered to a subject, the nanoparticle comprising:

at least one inner core that comprises a magnetic material having a Curie temperature that is the maximum temperature to which the inner core can be magnetically heated by RF energy, wherein the Curie temperature of the magnetic material is between 100 degrees Celsius and 1000 degrees Celsius; and a phase-change-material layer that surrounds the inner core and that comprises a phase-change material that is configured to absorb latent heat of fusion by undergoing a phase change selected from the group consisting of: solid to liquid, and gel to liquid, the phase-change occurring at a phase-change temperature that is between 42 and 80 degrees Celsius and is lower than the Curie temperature.

2. The nanoparticle according to claim 1, further comprising an outer layer disposed around the phase-change-material layer, the outer layer comprising a plurality of nano-subparticles that are separated from one another, so as to form a segmented layer.

3. The nanoparticle according to claim 2, wherein the subject includes a subject suffering from cancer, a body of the subject containing cancerous cells and non-cancerous cells, and wherein the nanoparticle is configured to amass in a vicinity of the cancer cells.

4. A nanoparticle for use with an alternating current radiofrequency (RF) heating device, the nanoparticle configured to be intravenously administered to a subject, the nanoparticle comprising:

a plurality of inner cores that comprise a magnetic material having a Curie temperature that is the maximum temperature to which the inner cores can be magnetically heated by RF energy, wherein the Curie temperature of the magnetic material is between 100 degrees Celsius and 1000 degrees Celsius; and a phase-change material (a) that surrounds the plurality of inner cores such that the plurality of inner cores are interspersed within the phase-change material, and (b) that is configured to absorb latent heat of fusion by undergoing a phase change selected from the group consisting of: solid to liquid, and gel to liquid, the phase-change occurring at a phase-change temperature that is between 42 and 80 degrees Celsius and is lower than the Curie temperature.

5. The nanoparticle according to claim 1, wherein the phase-change material is configured to undergo the selected phase change at a phase-change temperature of between 42 degrees Celsius and 60 degrees Celsius.

6. The nanoparticle according to claim 1, wherein the phase-change material is configured to undergo the selected phase change at a phase-change temperature of between 60 degrees Celsius and 80 degrees Celsius.

7. The nanoparticle according to claim 1, wherein the phase-change material is configured to prevent tissue that surrounds the nanoparticle from being heated to a temperature that is greater than the phase change temperature, by absorbing latent heat of fusion.

8. The nanoparticle according to claim 2, wherein the inner core is toxic, and wherein the nano-subparticles are configured to shield a body of the subject from toxicity of the inner core.

9. The nanoparticle according to claim 2, wherein the nano-subparticles comprise at least one metal.

10. The nanoparticle according to claim 9, wherein the nano-subparticles comprise nano-spheres of the at least one metal.

11. The nanoparticle according to claim 2, wherein the nano-subparticles comprise gold nano-subparticles.

12. The nanoparticle according to claim 1, wherein, due to relative thermal masses of the inner core and the phase-change-material layer in the nanoparticle, the phase-change material does not undergo a complete phase change, even if the inner core is subjected to continuous heating by the alternating current RF heating device.

13. The nanoparticle according to claim 1, wherein the nanoparticle is elongatable into an ellipsoid, such that when the nanoparticle is maximally elongated:

each of the semi-axes defined by the ellipsoid is greater than 5 nm, and at least two of the semi axes of the ellipsoid are less than 30 nm.

14. The nanoparticle according to claim 13, wherein the nanoparticle is configured to become elongated in response to hydrostatic pressure within a body of the subject.

15. The nanoparticle according to claim 13, wherein the nanoparticle is configured to become elongated in response to osmotic pressure within a body of the subject.

16. The nanoparticle according to claim 2, wherein the nanoparticle further comprises a plurality of polymer chains disposed around the outer layer, masking the outer layer, the phase-change-material layer, and the at least one inner core, thereby preventing breakdown of the nanoparticle.

17. The nanoparticle according to claim 16, wherein the polymer chains comprise chains of a polymer selected from the group consisting of: polyetheramine, polypropylene, and polyethylene glycol.

18. The nanoparticle according to claim 16, wherein the polymer chains are configured to at least partially mask at least the outer layer from phagocytic cells of a mononuclear phagocyte system of the subject.

19. The nanoparticle according to claim 1, wherein the phase-change material is organic.

20. The nanoparticle according to claim 19, wherein the organic phase-change material comprises paraffin.

21. The nanoparticle according to claim 4, further comprising an outer layer disposed around the phase-change-material, the outer layer comprising a plurality of nano-subparticles that are separated from one another, so as to form a segmented layer.

22. The nanoparticle according to claim 21, wherein the nano-subparticles comprise at least one metal.

23. The nanoparticle according to claim 21, wherein the subject includes a subject suffering from cancer, a body of the subject containing cancerous cells and non-cancerous cells, and wherein the nanoparticle is configured to amass in a vicinity of the cancer cells.

24. The nanoparticle according to claim 4, wherein the phase-change material is configured to prevent tissue that surrounds the nanoparticle from being heated to a temperature that is greater than the phase change temperature, by absorbing latent heat of fusion.

25. The nanoparticle according to claim 4, wherein the phase-change material is organic.

26. The nanoparticle according to claim 25, wherein the organic phase-change material comprises paraffin.

27. The nanoparticle according to claim 4, wherein the phase-change material is configured not to undergo a complete phase change, due to relative thermal masses of the plurality of inner cores and the phase-change material that surrounds the plurality of the inner cores, such that tissue of the subject that surrounds the nanoparticle is heated to the phase-change temperature of the phase-change material, but is not exposed to a temperature that is greater than the phase-change temperature.

28. The nanoparticle according to claim 4, wherein the magnetic material comprises iron oxide ($Fe_3O_4$).

29. The nanoparticle according to claim 2, wherein the nano-subparticles comprise nano-spheres.

30. The nanoparticle according to claim 2, wherein the nano-subparticles are made of a non-metallic biocompatible substance.

31. The nanoparticle according to claim 1, wherein the magnetic material comprises iron oxide ($Fe_3O_4$).

32. The nanoparticle according to claim 21, wherein the nano-subparticles comprise nano-spheres.

33. The nanoparticle according to claim 21, wherein the nano-subparticles are made of a non-metallic biocompatible substance.

34. The nanoparticle according to claim 1, wherein the phase-change material is configured not to undergo a complete phase change, due to relative thermal masses of the at least one inner core and the phase-change-material layer in the nanoparticle, such that tissue of the subject that surrounds the nanoparticle is heated to the phase-change temperature of the phase-change material, but is not exposed to a temperature that is greater than the phase-change temperature.

* * * * *